(12) United States Patent
Cormier

(10) Patent No.: US 8,088,748 B2
(45) Date of Patent: Jan. 3, 2012

(54) ANTISENSE RESPIRATORY SYNCYTIAL VIRUS VACCINE AND THERAPY

(75) Inventor: Stephania Cormier, Slidell, LA (US)

(73) Assignee: The Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 241 days.

(21) Appl. No.: 12/259,155

(22) Filed: Oct. 27, 2008

(65) Prior Publication Data

US 2010/0203069 A1     Aug. 12, 2010

Related U.S. Application Data

(60) Provisional application No. 60/983,040, filed on Oct. 26, 2007.

(51) Int. Cl.
*C12N 15/11* (2006.01)
*C07H 21/07* (2006.01)
*A61K 39/155* (2006.01)

(52) U.S. Cl. .................. 514/44 A; 424/211.1; 536/24.5

(58) Field of Classification Search ....................... None
See application file for complete search history.

(56) References Cited

OTHER PUBLICATIONS

Karras et al (Am J Respir Cell Mol Biol vol. 36. pp. 276-285, Sep. 21, 2006).*
Becker (Virus Genes 33:235-252, 2006).*
Ripple et al (J. Immunol. 185: 4804-4811, 2010).*

* cited by examiner

*Primary Examiner* — Richard Schnizer
(74) *Attorney, Agent, or Firm* — Jason P. Mueller; Adams and Reese LLP

(57) ABSTRACT

A method is provided for immunizing against pulmonary inflammation and airway hyperresponsiveness associated with infantile RSV infection. This method includes administering an antisense oligonucletide to a subject in need thereof.

24 Claims, 11 Drawing Sheets

```
Human     KVLQEPTCVSDYMSISTCEWKMNGPTNCSTELRLLYQLV.FLLSEAHTCI PEN NG...GAGCVCHLLMDD
Macaque   KVLQEPACVSDYMSISTCEWKMGGPTNCSAELRLLYQLV.FQSSETHTCV PEN NG...GVGCVCHLLMDD
Mouse     KVLGEPTCFSDYIRTSTCEWFLDSAVDCSSQLCLHYRLMFFEFSENLTCI PRN SA...STVCVCHMEMNR
Bovine    RVLQDPTCFSDYISNSTCEWEMAGPTNCRAELHLSYQLN.FYYSENHTCV PEN RAGVGGTVCICHMLTEN Human     VVSADNYTLDLWAGQQLLWKGSFKPSEHV
Macaque   VVSMDNYTLDLWAGQQLLWKGSFKPSEHV
Mouse     PVQSDRYQMELWAEHRQLWQGSFSPSGNV
Bovine    PVRQDIYQLDLWAGKQLLWNSSFKPSEHV
```

FIG. 12

SEQUENCE LISTING

```
<160> NUMBER OF SEQ ID NOS: 10

<210> SEQ ID NO 1
<211> LENGTH: 3597
<212> TYPE: DNA
<213> ORGANISM: Homo sapiens

<400> SEQUENCE: 1
ggcgaatgga gcaggggcgc gcagataatt aaagatttac acacagctgg aagaaatcat      60
agagaagccg ggcgtggtgg ctcatgccta taatcccagc acttttggag gctgaggcgg     120
gcagatcact tgagatcagg agttcgagac cagcctggtg ccttggcatc tcccaatggg     180
gtggctttgc tctgggctcc tgttccctgt gagctgcctg gtcctgctgc aggtggcaag     240
ctctgggaac atgaaggtct tgcaggagcc cacctgcgtc tccgactaca tgagcatctc     300
tacttgcgag tggaagatga atggtcccac caattgcagc accgagctcc gcctgttgta     360
ccagctggtt tttctgctct ccgaagccca cacgtgtatc cctgagaaca acggaggcgc     420
ggggtgcgtg tgccacctgc tcatggatga cgtggtcagt gcggataact atacactgga     480
cctgtgggct gggcagcagc tgctgtggaa gggctccttc aagcccagcg agcatgtgaa     540
acccagggcc ccaggaaacc tgacagttca caccaatgtc tccgacactc tgctgctgac     600
ctggagcaac ccgtatcccc ctgacaatta cctgtataat catctcacct atgcagtcaa     660
catttggagt gaaaacgacc cggcagattt cagaatctat aacgtgacct acctagaacc     720
ctccctccgc atcgcagcca gcaccctgaa gtctgggatt tcctacaggg cacgggtgag     780
ggcctgggct cagtgctata acaccacctg gagtgagtgg agccccagca ccaagtggca     840
```

-continued

```
caactcctac agggagccct tcgagcagca cctcctgctg ggcgtcagcg tttcctgcat    900
tgtcatcctg gccgtctgcc tgttgtgcta tgtcagcatc accaagatta agaaagaatg    960
gtgggatcag attcccaacc cagcccgcag ccgcctcgtg gctataataa tccaggatgc   1020
tcaggggtca cagtgggaga gcggtcccg aggccaggaa ccagccaagt gcccacactg    1080
gaagaattgt cttaccaagc tcttgccctg ttttctggag cacaacatga aagggatga    1140
agatcctcac aaggctgcca aagagatgcc tttccagggc tctggaaaat cagcatggtg   1200
cccagtggag atcagcaaga cagtcctctg ccagagagc atcagcgtgg tgcgatgtgt    1260
ggagttgttt gaggccccgg tggagtgtga ggaggaggag gaggtagagg aagaaaaagg   1320
gagcttctgt gcatcgccct agagcagcag ggatgacttc caggagggaa gggagggcat   1380
tgtggcccgg ctaacagaga gcctgttcct ggacctgctc ggagaggaga atggggctt    1440
ttgccagcag gacatggggg agtcatgcct tcttccacct tcgggaagta cgagtgctca   1500
catgccctgg gatgagttcc caagtgcagg gcccaaggag gcacctccct ggggcaagga   1560
gcagcctctc cacctggagc caagtcctcc tgccagcccg acccagagtc cagacaacct   1620
gacttgcaca gagacgcccc tcgtcatcgc aggcaaccct gcttaccgca gcttcagcaa   1680
ctccctgagc cagtcaccgt gtcccagaga gctgggtcca gacccactgc tggccagaca   1740
cctggaggaa gtagaacccg agatgccctg tgtcccccag ctctctgagc caaccactgt   1800
gccccaacct gagccagaaa cctgggagca gatcctccgc cgaaatgtcc tccagcatgg   1860
ggcagctgca gccccgtct cggccccac cagtggctat caggagtttg tacatgcggt     1920
ggagcagggt ggcacccagg ccagtgcggt ggtgggcttg ggtcccccag agaggctgg    1980
ttacaaggcc ttctcaagcc tgcttgccag cagtgctgtg tcccagaga aatgtgggtt    2040
tggggctagc agtggggaag aggggtataa gcctttccaa gacctcattc ctggctgccc   2100
tggggaccct gccccagtcc ctgtcccctt gttcaccttt ggactggaca gggagccacc   2160
tcgcagtccg cagagctcac atctcccaag cagctcccca gagcacctgg gtctggagcc   2220
ggggaaaag gtagaggaca tgccaaagcc cccacttccc caggagcagg ccacagaccc    2280
ccttgtggac agcctgggca gtggcattgt ctactcagcc cttacctgcc acctgtgcgg   2340
ccacctgaaa cagtgtcatg gcaggagga tggtggccag accctgtca tggccagtcc     2400
ttgctgtggc tgctgctgtg gagacaggtc ctcgccccct acaaccccc tgagggcccc    2460
agacccctct ccaggtgggg ttccactgga ggccagtctg tgtccggcct ccctggcacc   2520
ctcgggcatc tcagagaaga gtaaatcctc atcatccttc catcctgccc ctggcaatgc   2580
tcagagctca agccagaccc ccaaaatcgt gaactttgtc tccgtgggac ccacatacat   2640
gagggtctct taggtgcatg tcctcttgtt gctgagtctg cagatgagga ctagggctta   2700
tccatgcctg ggaaatgcca cctcctggaa ggcagccagg ctggcagatt ccaaaagac    2760
ttgaagaacc atggtatgaa ggtgattggc cccactgacg ttggcctaac actgggctgc   2820
agagactgga ccccgcccag cattgggctg ggctcgccac atcccatgag agtagagggc   2880
actgggtcgc cgtgccccac ggcaggcccc tgcaggaaaa ctgaggccct tgggcacctc   2940
gacttgtgaa cgagttgttg gctgctccct ccacagcttc tgcagcagac tgtccctgtt   3000
gtaactgccc aaggcatgtt ttgcccacca gatcatggcc cacgtggagg cccacctgcc   3060
tctgtctcac tgaactagaa gccgagccta gaaactaaca cagccatcaa gggaatgact   3120
tgggcggcct tggaaaatcg atgagaaatt gaacttcagg gagggtggtc attgcctaga   3180
ggtgctcatt catttaacag agcttcctta ggttgatgct ggaggcagaa tcccggctgt   3240
```

| | |
|---|---:|
| caaggggtgt tcagttaagg ggagcaacag aggacatgaa aaattgctat gactaaagca | 3300 |
| gggacaattt gctgccaaac acccatgccc agctgtatgg ctgggggctc ctcgtatgca | 3360 |
| tggaaccccc agaataaata tgctcagcca ccctgtgggc cgggcaatcc agacagcagg | 3420 |
| cataaggcac cagttaccct gcatgttggc ccagacctca ggtgctaggg aaggcgggaa | 3480 |
| ccttgggttg agtaatgctc gtctgtgtgt tttagtttca tcacctgtta tctgtgtttg | 3540 |
| ctgaggagag tggaacagaa ggggtggagt tttgtataaa taaagtttct ttgtctc | 3597 |

```
<210> SEQ ID NO 2
<211> LENGTH: 3697
<212> TYPE: DNA
<213> ORGANISM: Mus musculus

<400> SEQUENCE: 2
```

| | |
|---|---:|
| cgcaggaaag ccccgcgcgg cgcgtggagc ctgaactcgc aggttctggc tggacttctc | 60 |
| gaagctgagg agaagcagag ggacctggct tctgattttg gatctgcgtg cttgctggtt | 120 |
| ctggcgcctg ctggtcttgt tcctgtaacc taggactcgg ggcttgcaca tgctttttt | 180 |
| ttgaagttgc tggagaggga gcccaggacc ttgtgcaggc accttttgtg tccccaatgg | 240 |
| ggcggctttg caccaagttc ctgacctctg tgggctgtct gattttgctg ttggtgactg | 300 |
| gatctgggag catcaaggtc ctgggtgagc ccacctgctt ctctgactac atccgcactt | 360 |
| ccacgtgtga gtggttcctg gatagcgctg tggactgcag ttctcagctc tgcctacact | 420 |
| acaggctgat gttcttcgag ttctctgaaa acctcacatg catcccgagg aacagtgcca | 480 |
| gcactgtgtg tgtgtgccac atggaaatga ataggccggt ccaatcagac agataccaga | 540 |
| tggaactgtg ggctgagcac agacagctgt ggcagggctc cttcagcccc agtggtaatg | 600 |
| tgaagcccct agctccagac aacctcacac tccacaccaa tgtgtccgac gaatggctgc | 660 |
| tgacctggaa taacctgtac ccatcgaaca acttactgta caagacctc atctccatgg | 720 |
| tcaacatctc cagagaggac aaccctgcag aattcatagt ctataatgtg acctacaagg | 780 |
| aacccaggct gagcttcccg atcaacatcc tgatgtcagg ggtctactat acggcgcgtg | 840 |
| tgagggtcag atcccagata ctcactggca cctggagtga gtggagtcct agcatcacgt | 900 |
| ggtacaaccc aagtaatgaa aatctgtgac tgagtgacct tggggctgc ggtggtgagg | 960 |
| agagctcacg ggaatcctgg agcagtgtag ctggcgtgtc aaaagcagaa acgcaggaga | 1020 |
| tggacttcca gctgcccctg atacagcgcc ttccactggg ggtcaccatc tcctgcctct | 1080 |
| gcatcccgtt gttttgcctg ttctgttact tcagcattac caagattaag aagatatggt | 1140 |
| gggaccagat tcccacccca gcacgcagtc ccttggtggc catcatcatt caggatgcac | 1200 |
| aggtgccccct ctgggataag cagacccgaa gccaggagtc aaccaagtac ccgcactgga | 1260 |
| aaacttgtct agacaagctg ctgccttgct tgctgaagca cagagtaaag aagaagacag | 1320 |
| acttcccgaa ggctgcccca accaagtctc tccagagtcc tggaaaggca ggctggtgtc | 1380 |
| ccatggaggt cagcaggacc gtcctctggc cagagaatgt tagtgtcagt gtggtgcgct | 1440 |
| gtatggagct gtttgaggcc ccagtacaga atgtggagga ggaagaagat gagatagtca | 1500 |
| aagaggacct gagcatgtca cctgagaaca gcggaggctg cggcttccag gagagccagg | 1560 |
| cagacatcat ggctcggctc actgagaacc tgttttccga cttgttggag ctgagaatg | 1620 |
| ggggccttgg ccagtcagcc ttggcagagt catgctcccc tctgccttca ggaagtgggc | 1680 |
| aggcttctgt atcctgggcc tgcctcccca tggggcccag tgaggaggcc acatgccagg | 1740 |
| tcacagagca gccttcacac ccaggccctc tttcaggcag cccagcccag agtgcaccta | 1800 |

| | |
|---|---|
| ctctggcttg cacgcaggtc ccacttgtcc ttgcagacaa tcctgcctac cggagtttta | 1860 |
| gtgactgctg tagcccggcc ccaaatcctg gagagctggc tccagagcag cagcaggctg | 1920 |
| atcatctgga agaagaggag cctccaagcc cggctgaccc ccattcttca gggccaccaa | 1980 |
| tgcagccagt ggagagctgg gagcagatcc ttcacatgag tgtcctgcag catggggcag | 2040 |
| ctgctggctc caccccagcc cctgccggtg ctaccagga gtttgtgcag gcagtgaagc | 2100 |
| agggtgccgc ccaggatcct ggggtgcctg tgtcaggcc ttctggagac cccgttaca | 2160 |
| aggccttctc gagcctgctc agcagcaatg gcatccgcgg gacacagca gcagcgggga | 2220 |
| ctgacgatgg gcatggaggc tacaagccct tccagaatcc tgttcctaac cagtcccta | 2280 |
| gctccgtgcc cttatttact ttcggactag acacggagct gtcacccagt cctctgaact | 2340 |
| cagacccacc caaaagcccc ccagaatgcc ttggtctgga ctggggctc aaaggaggtg | 2400 |
| actgggtgaa ggcccctcct cctgcagatc aggtgcccaa gccctttggg gatgacctgg | 2460 |
| gctttggtat tgtgtactcg tccctcactt gccacttgtg tggccacctg aagcaacacc | 2520 |
| acagccagga ggaaggtggc cagagcccca tcgttgctag ccctggctgt ggctgctgct | 2580 |
| acgatgacag atcaccatcc ctggggagcc tctcggggggc cttggaaagc tgtcctgagg | 2640 |
| gaataccacc agaagccaac ctcatgtcag cacccaagac accctcaaac ttgtcagggg | 2700 |
| agggcaaggg ccctggtcac tctcctgttc ccagccagac gaccgaggtg cctgtgggcg | 2760 |
| ccctgggcat tgctgtttct taggtgagtg agtgtgctgt tgttgctgag gtctgtgctg | 2820 |
| aggccagggt tcctccaagc cagggaagta cttcctggga gacagccag ctggcaggtt | 2880 |
| tcccagaaat ccagagaatg gtgaattgaa gatgtaaact tggcctgacc ctggacgctc | 2940 |
| ggagcctggc tgtctcctct tccactggcc tgggctctcc tccctcccaa gggatacagg | 3000 |
| ggctcactgt gcttggtccc acagcagtgc tgacgttcct aagtcctggg ctttcctagc | 3060 |
| tgatgttgtc ctacctactc agtcccattt tgtccaccga atagacctgt cactcaaggc | 3120 |
| tctcagcggt cctgccatag ctgctggacg ctcccagctg gaagctgggc ctagaaactc | 3180 |
| acagatggcc tggcagtggc atgggaggcc ctaaaaatta gtggaaattt tgagagagga | 3240 |
| caggtattgc cccacagagg ccattcattg aacagccagg actgggacta gaggcagagc | 3300 |
| ctgctgtcct ccgctcagtt gtagaaagca acaaggacac aaacttgatt gcccaaagtc | 3360 |
| actgccagtt acccacatat gaccagaagc cagggctcct gggatgtgga agataaacaa | 3420 |
| acacagttgc cgggtggcag ggccccagcg ggcacgataa ctggcagtca aggcgatacc | 3480 |
| tcgagggaac tgtgggggctg gtcctggttg gtggtcaggt ggtagggata gcagatggca | 3540 |
| gactttggtg agtgagtgag tctgactgtg ttctggaaga tgggaccggg ctcagcactg | 3600 |
| tctgctcacg tccccactgt tgcaacacct agtctgtttg caaggaggac aggacaggtc | 3660 |
| acatggagct ttatgtcaat aaagtctttta tcttgtc | 3697 |

<210> SEQ ID NO 3
<211> LENGTH: 20
<212> TYPE: DNA
<213> ORGANISM: Artificial
<220> FEATURE:
<223> OTHER INFORMATION: Antisense compound
<220> FEATURE:
<221> NAME/KEY: misc_feature
<222> LOCATION: (1)...(5)
<223> OTHER INFORMATION: 2'-o-methoxyethyl
<220> FEATURE:
<221> NAME/KEY: misc_feature
<222> LOCATION: (1)...(20)
<223> OTHER INFORMATION: phosphorothioate
<220> FEATURE:

```
<221> NAME/KEY: misc_feature
<222> LOCATION: (16)...(20)
<223> OTHER INFORMATION: 2'-0-methoxyethyl

<400> SEQUENCE: 3
ccgctgttct caggtgacat                                              20

<210> SEQ ID NO 4
<211> LENGTH: 20
<212> TYPE: DNA
<213> ORGANISM: Artificial
<220> FEATURE:
<223> OTHER INFORMATION: Antisense compound
<220> FEATURE:
<221> NAME/KEY: misc_feature
<222> LOCATION: (1)...(5)
<223> OTHER INFORMATION: 2'-o-methoxyethyl
<220> FEATURE:
<221> NAME/KEY: misc_feature
<222> LOCATION: (1)...(20)
<223> OTHER INFORMATION: phosphorothioate
<220> FEATURE:
<221> NAME/KEY: misc_feature
<222> LOCATION: (16)...(20)
<223> OTHER INFORMATION: 2'-D-methozyethyl

<400> SEQUENCE: 4
ccactcatca ctgctgactt                                              20

<210> SEQ ID NO 5
<211> LENGTH: 825
<212> TYPE: PRT
<213> ORGANISM: Homo sapiens

<400> SEQUENCE: 5
```

| | | | | | | | | | | | | | | |
|---|---|---|---|---|---|---|---|---|---|---|---|---|---|---|
| Met | Gly | Trp | Leu | Cys | Ser | Gly | Leu | Leu | Phe | Pro | Val | Ser | Cys | Val |
| 1 | | | | 5 | | | | | 10 | | | | | 15 |
| Leu | Leu | Gln | Val | Ala | Ser | Ser | Gly | Asn | Met | Lys | Val | Leu | Gln | Glu | Pro |
| | | | 20 | | | | | 25 | | | | | 30 | | |
| Thr | Cys | Val | Ser | Asp | Tyr | Met | Ser | Ile | Ser | Thr | Cys | Glu | Trp | Lys | Met |
| | | 35 | | | | | 40 | | | | | 45 | | | |
| Asn | Gly | Pro | Thr | Asn | Cys | Ser | Thr | Glu | Leu | Arg | Leu | Leu | Tyr | Gln | Leu |
| 50 | | | | | 55 | | | | | 60 | | | | | |
| Val | Phe | Leu | Leu | Ser | Glu | Ala | His | Thr | Cys | Ile | Pro | Glu | Asn | Asn | Gly |
| 65 | | | | | 70 | | | | | 75 | | | | | 80 |
| Gly | Ala | Gly | Cys | Val | Cys | His | Leu | Leu | Met | Asp | Asp | Val | Val | Ser | Ala |
| | | | | 85 | | | | | 90 | | | | | 95 | |
| Asp | Asn | Tyr | Thr | Leu | Asp | Leu | Trp | Ala | Gly | Gln | Gln | Leu | Leu | Trp | Lys |
| | | | 100 | | | | | 105 | | | | | 110 | | |
| Gly | Ser | Phe | Lys | Pro | Ser | Glu | His | Val | Lys | Pro | Arg | Ala | Pro | Gly | Asn |
| | | | 115 | | | | | 120 | | | | | 125 | | |
| Leu | Thr | Val | His | Thr | Asn | Val | Ser | Asp | Thr | Leu | Leu | Leu | Thr | Trp | Ser |
| | 130 | | | | | 135 | | | | | 140 | | | | |
| Asn | Pro | Tyr | Pro | Pro | Asp | Asn | Tyr | Leu | Tyr | Asn | His | Leu | Thr | Tyr | Ala |
| 145 | | | | | 150 | | | | | 155 | | | | | 160 |
| Val | Asn | Ile | Trp | Ser | Glu | Asn | Asp | Pro | Ala | Asp | Phe | Arg | Ile | Tyr | Asn |
| | | | | 165 | | | | | 170 | | | | | 175 | |
| Val | Thr | Tyr | Leu | Glu | Pro | Ser | Leu | Arg | Ile | Ala | Ala | Ser | Thr | Leu | Lys |
| | | | 180 | | | | | 185 | | | | | 190 | | |
| Ser | Gly | Ile | Ser | Tyr | Arg | Ala | Arg | Val | Arg | Ala | Trp | Ala | Gln | Cys | Tyr |
| | | | 195 | | | | | 200 | | | | | 205 | | |
| Asn | Thr | Thr | Trp | Ser | Glu | Trp | Ser | Pro | Ser | Thr | Lys | Trp | His | Asn | Ser |

-continued

```
              210                 215                 220
Tyr Arg Glu Pro Phe Glu Gln His Leu Leu Gly Val Ser Val Ser
225                 230                 235                 240

Cys Ile Val Ile Leu Ala Val Cys Leu Leu Cys Tyr Val Ser Ile Thr
                    245                 250                 255

Lys Ile Lys Lys Glu Trp Trp Asp Gln Ile Pro Asn Pro Ala Arg Ser
                    260                 265                 270

Arg Leu Val Ala Ile Ile Gln Asp Ala Gln Gly Ser Gln Trp Glu
                275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                    325                 330                 335

Gly Lys Ser Ala Trp Cys Pro Val Glu Ile Ser Lys Thr Val Leu Trp
                340                 345                 350

Pro Glu Ser Ile Ser Val Val Arg Cys Val Glu Leu Phe Glu Ala Pro
                355                 360                 365

Val Glu Cys Glu Glu Glu Glu Val Glu Glu Glu Lys Gly Ser Phe
370                 375                 380

Cys Ala Ser Pro Glu Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                    405                 410                 415

Glu Glu Asn Gly Gly Phe Cys Gln Gln Asp Met Gly Glu Ser Cys Leu
                420                 425                 430

Leu Pro Pro Ser Gly Ser Thr Ser Ala His Met Pro Trp Asp Glu Phe
                435                 440                 445

Pro Ser Ala Gly Pro Lys Glu Ala Pro Pro Trp Gly Lys Glu Gln Pro
450                 455                 460

Leu His Leu Glu Pro Ser Pro Pro Ala Ser Pro Thr Gln Ser Pro Asp
465                 470                 475                 480

Asn Leu Thr Cys Thr Glu Thr Pro Leu Val Ile Ala Gly Asn Pro Ala
                    485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Val Glu Pro
                515                 520                 525

Glu Met Pro Cys Val Pro Gln Leu Ser Glu Pro Thr Thr Val Pro Gln
530                 535                 540

Pro Glu Pro Glu Thr Trp Glu Gln Ile Leu Arg Arg Asp Val Leu Gln
545                 550                 555                 560

His Gly Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
                580                 585                 590

Val Gly Leu Gly Pro Pro Gly Glu Ala Gly Tyr Lys Ala Phe Ser Ser
                595                 600                 605

Leu Leu Ala Ser Ser Ala Val Ser Pro Glu Lys Cys Gly Phe Gly Ala
                610                 615                 620

Ser Ser Gly Glu Glu Gly Tyr Lys Pro Phe Gln Asp Leu Ile Pro Gly
625                 630                 635                 640
```

```
Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
            660                 665                 670

Ser Ser Pro Glu His Leu Gly Leu Glu Pro Gly Glu Lys Val Glu Asp
        675                 680                 685

Met Pro Lys Pro Pro Leu Pro Gln Glu Gln Ala Thr Asp Pro Leu Val
    690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
            740                 745                 750

Ser Pro Pro Thr Thr Pro Leu Arg Ala Pro Asp Pro Ser Pro Gly Gly
        755                 760                 765

Val Pro Leu Glu Ala Ser Leu Cys Pro Ala Ser Leu Ala Pro Ser Gly
    770                 775                 780

Ile Ser Glu Lys Ser Lys Ser Ser Ser Phe His Pro Ala Pro Gly
785                 790                 795                 800

Asn Ala Gln Ser Ser Gln Thr Pro Lys Ile Val Asn Pro Val Ser
                805                 810                 815

Val Gly Pro Thr Tyr Met Arg Val Ser
            820                 825

<210> SEQ ID NO 6
<211> LENGTH: 731
<212> TYPE: PRT
<213> ORGANISM: Macaca mulatta

<400> SEQUENCE: 6

Met Gly Trp Leu Cys Ser Gly Leu Leu Phe Pro Val Ser Cys Leu Val
1               5                   10                  15

Leu Leu Gln Val Ala Ser Ser Gly Ser Met Lys Val Leu Gln Glu Pro
            20                  25                  30

Ala Cys Val Ser Asp Tyr Met Ser Ile Ser Thr Cys Glu Trp Lys Met
        35                  40                  45

Gly Gly Pro Thr Asn Cys Ser Ala Glu Leu Arg Leu Leu Tyr Gln Leu
    50                  55                  60

Val Phe Gln Ser Ser Glu Thr His Thr Cys Val Pro Glu Asn Asp Gly
65                  70                  75                  80

Gly Val Gly Cys Val Cys His Leu Leu Met Asp Asp Val Val Ser Met
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Val Leu Leu Thr Trp Ser
    130                 135                 140

Asn Pro Tyr Pro Pro Asp Asn Tyr Leu Tyr Asn Asp Leu Thr Tyr Ala
145                 150                 155                 160

Val Asp Ile Trp Ser Glu Asn Asp Pro Ala Tyr Ser Arg Ile His Asn
                165                 170                 175

Val Thr Tyr Leu Lys Pro Thr Leu Arg Ile Pro Ala Ser Thr Leu Lys
            180                 185                 190
```

-continued

```
Ser Gly Ile Ser Tyr Arg Ala Arg Val Arg Ala Trp Ala Gln His Tyr
        195                 200                 205

Asn Thr Thr Trp Ser Glu Trp Ser Pro Ser Thr Lys Trp Tyr Asn Ser
        210                 215                 220

Tyr Arg Glu Pro Phe Glu Gln Arg Leu Leu Trp Gly Val Ser Ala Ala
225                 230                 235                 240

Cys Val Phe Ile Leu Phe Phe Cys Leu Ser Lys Tyr Phe Ser Val Thr
                245                 250                 255

Lys Ile Lys Lys Glu Trp Trp Asp Gln Ile Pro Asp Pro Ala Arg Ser
                260                 265                 270

His Leu Val Ala Ile Ile Gln Asp Ala Gln Glu Ser Gln Trp Glu
        275                 280                 285

Lys Arg Ser Arg Gly Gln Glu Ala Ala Lys Cys Pro Tyr Trp Lys Asp
        290                 295                 300

Cys Leu Thr Lys Leu Leu Pro Cys Phe Leu Glu His Asp Met Lys Arg
305                 310                 315                 320

Asp Glu Asp Pro His Lys Ala Val Lys Asp Leu Pro Phe Arg Gly Ser
                325                 330                 335

Gly Lys Ser Ala Trp Cys Pro Val Glu Ile Ser Lys Thr Val Leu Trp
                340                 345                 350

Pro Glu Ser Ile Ser Val Val Arg Cys Val Glu Leu Phe Glu Ala Pro
        355                 360                 365

Val Glu Cys Lys Glu Glu Glu Val Glu Glu Lys Gly Ser Phe
        370                 375                 380

Cys Thr Ser Ser Glu Ser Asn Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Gly Glu Asn Gly Gly Phe Phe Gln Gln Asp Met Gly Glu Ser Cys Leu
                420                 425                 430

Leu Pro Pro Leu Gly Ser Thr Ser Ala His Val Pro Trp Asp Glu Phe
        435                 440                 445

Pro Ser Ala Gly Pro Lys Glu Val Pro Pro Trp Gly Lys Glu Gln Pro
        450                 455                 460

Leu His Gln Glu Pro Ser Pro Pro Ala Ser Pro Thr Gln Ser Pro Asp
465                 470                 475                 480

Asn Pro Thr Cys Thr Glu Met Pro Leu Val Ile Ser Ser Asn Pro Ala
                485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Cys Gly Phe
        515                 520                 525

Gly Ala Ser Ser Gly Glu Glu Gly Tyr Lys Pro Phe Gln Asp Leu Thr
        530                 535                 540

Pro Gly Cys Pro Gly Asp Pro Ala Pro Val Pro Val Pro Leu Phe Thr
545                 550                 555                 560

Phe Gly Leu Asp Arg Glu Pro Pro His Ser Pro Gln Ser His Leu
                565                 570                 575

Pro Ser Asn Ser Pro Glu His Leu Ala Leu Glu Pro Gly Glu Lys Val
                580                 585                 590

Glu Asp Met Gln Lys Pro Pro Leu Pro Pro Glu Gln Ala Thr Asp Pro
        595                 600                 605

Leu Gly Asp Asp Leu Gly Ser Gly Ile Val Tyr Ser Ala Leu Thr Cys
        610                 615                 620
```

His Leu Cys Gly His Leu Lys Gln Cys His Gly Gln Glu Asp Gly Gly
625                 630                 635                 640

Gln Ala Pro Val Val Ala Ser Pro Cys Gly Cys Cys Cys Gly Asp
            645                 650                 655

Arg Ser Ser Pro Pro Thr Thr Pro Leu Arg Ala Pro Asp Pro Ser Leu
            660                 665                 670

Gly Gly Val Pro Leu Glu Ala Ser Leu Cys Pro Ala Ser Leu Ala Pro
            675                 680                 685

Ser Gly Ile Ser Glu Lys Ser Lys Ser Ser Leu Ser Phe His Pro Ala
            690                 695                 700

Pro Gly Ser Ala Gln Ser Ser Ser Gln Thr Pro Gln Ile Val Asn Phe
705                 710                 715                 720

Val Ser Val Gly Pro Thr Cys Met Arg Val Ser
                725                 730

<210> SEQ ID NO 7
<211> LENGTH: 810
<212> TYPE: PRT
<213> ORGANISM: Mus musculus

<400> SEQUENCE: 7

Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gly Glu Pro
                20                  25                  30

Thr Lys Phe Ser Asp Tyr Ile Arg Thr Ser Thr Cys Glu Trp Phe Leu
            35                  40                  45

Asp Ser Ala Val Asp Cys Ser Ser Gln Leu Cys Leu His Tyr Arg Leu
50                  55                  60

Met Phe Phe Glu Phe Ser Glu Asp Leu Thr Cys Ile Pro Arg Asn Ser
65                  70                  75                  80

Ala Ser Thr Val Cys Val Cys His Met Glu Met Asn Arg Pro Val Gln
                85                  90                  95

Ser Asp Arg Tyr Gln Met Glu Leu Trp Ala Glu His Arg Gln Leu Trp
            100                 105                 110

Gln Gly Ser Phe Ser Pro Ser Gly Asn Val Lys Pro Leu Ala Pro Asp
        115                 120                 125

Asp Leu Thr Leu His Thr Asn Val Ser Asp Glu Trp Leu Leu Thr Trp
130                 135                 140

Asn Asn Leu Tyr Pro Ser Asn Asp Leu Leu Tyr Lys Asp Leu Ile Ser
145                 150                 155                 160

Met Val Asn Ile Ser Arg Glu Asp Asn Pro Ala Glu Phe Ile Val Tyr
                165                 170                 175

Asn Val Thr Tyr Lys Glu Pro Arg Leu Ser Phe Pro Ile Asn Ile Leu
            180                 185                 190

Met Ser Gly Val Tyr Tyr Thr Ala Arg Val Arg Val Arg Ser Gln Ile
        195                 200                 205

Leu Thr Gly Thr Trp Ser Glu Trp Ser Pro Ser Ile Thr Trp Tyr Asn
210                 215                 220

His Pro Gln Leu Pro Leu Ile Gln Arg Leu Pro Leu Gly Val Thr Ile
225                 230                 235                 240

Ser Cys Leu Cys Ile Pro Leu Phe Cys Leu Phe Cys Tyr Phe Ser Ile
                245                 250                 255

Thr Lys Ile Lys Lys Ile Trp Trp Asp Gln Ile Pro Thr Pro Ala Arg
            260                 265                 270

```
Ser Pro Leu Val Ala Ile Ile Gln Asp Ala Gln Val Pro Leu Trp
    275                 280                 285
Asp Lys Gln Thr Arg Ser Gln Glu Ser Thr Lys Tyr Pro His Trp Lys
290                 295                 300
Thr Cys Leu Asp Lys Leu Leu Pro Cys Leu Leu Lys His Arg Val Lys
305                 310                 315                 320
Lys Lys Thr Asp Phe Pro Lys Ala Ala Pro Thr Lys Ser Leu Gln Ser
                325                 330                 335
Pro Gly Lys Ala Gly Trp Cys Pro Met Glu Val Ser Arg Thr Val Leu
                340                 345                 350
Trp Pro Glu Asn Val Ser Val Ser Val Arg Cys Met Glu Leu Phe
    355                 360                 365
Glu Ala Pro Val Gln Asn Val Glu Glu Glu Asp Glu Ile Val Lys
    370                 375                 380
Glu Asp Leu Ser Met Ser Pro Glu Asn Ser Gly Gly Cys Gly Phe Gln
385                 390                 395                 400
Glu Ser Gln Ala Asp Ile Met Ala Arg Leu Thr Glu Asn Leu Phe Ser
                405                 410                 415
Asp Leu Leu Glu Ala Glu Asn Gly Gly Leu Gly Gln Ser Ala Leu Ala
                420                 425                 430
Glu Ser Cys Ser Pro Leu Pro Ser Gly Ser Gln Ala Ser Val Ser
    435                 440                 445
Trp Ala Cys Leu Pro Met Gly Pro Ser Glu Glu Ala Thr Cys Gln Val
    450                 455                 460
Thr Glu Gln Pro Ser His Pro Gly Pro Leu Ser Gly Ser Pro Ala Gln
465                 470                 475                 480
Ser Ala Pro Thr Leu Ala Cys Thr Gln Val Pro Leu Val Leu Ala Asp
                485                 490                 495
Asp Pro Ala Tyr Arg Ser Phe Ser Asp Cys Cys Ser Pro Ala Pro Asn
                500                 505                 510
Pro Gly Glu Leu Ala Pro Glu Gln Gln Gln Ala Asp His Leu Glu Glu
                515                 520                 525
Glu Glu Pro Pro Ser Pro Ala Asp Pro His Ser Ser Gly Pro Pro Met
    530                 535                 540
Gln Pro Val Glu Ser Trp Glu Gln Ile Leu His Met Ser Val Leu Gln
545                 550                 555                 560
His Gly Ala Ala Ala Gly Ser Thr Pro Ala Pro Ala Gly Gly Tyr Gln
                565                 570                 575
Glu Phe Val Gln Ala Val Lys Gln Gly Ala Ala Gln Asp Pro Gly Val
                580                 585                 590
Pro Gly Val Arg Pro Ser Gly Asp Pro Gly Tyr Lys Ala Phe Ser Ser
                595                 600                 605
Leu Leu Ser Ser Asn Gly Ile Arg Gly Asp Thr Ala Ala Ala Gly Thr
                610                 615                 620
Asp Asp Gly His Gly Gly Tyr Lys Pro Phe Gln Asn Pro Val Pro Asn
625                 630                 635                 640
Gln Ser Pro Ser Ser Val Pro Leu Phe Thr Phe Gly Leu Asp Thr Glu
                645                 650                 655
Leu Ser Pro Ser Pro Leu Asn Ser Asp Pro Lys Ser Pro Pro Glu
    660                 665                 670
Cys Leu Gly Leu Glu Leu Gly Leu Lys Gly Gly Asp Trp Val Lys Ala
    675                 680                 685
Pro Pro Pro Ala Asp Gln Val Pro Lys Pro Phe Gly Asp Asp Leu Gly
```

```
            690                 695                 700
Phe Gly Ile Val Tyr Ser Ser Leu Thr Cys His Leu Cys Gly His Leu
705                 710                 715                 720

Lys Gln His His Ser Gln Glu Glu Gly Gly Gln Ser Pro Ile Val Ala
                725                 730                 735

Ser Pro Gly Cys Gly Cys Cys Tyr Asp Asp Arg Ser Pro Ser Leu Gly
            740                 745                 750

Ser Leu Ser Gly Ala Leu Glu Ser Cys Pro Glu Gly Ile Pro Pro Glu
            755                 760                 765

Ala Asn Leu Met Ser Ala Pro Lys Thr Pro Ser Asn Leu Ser Gly Glu
            770                 775                 780

Gly Lys Gly Pro Gly His Ser Pro Val Pro Ser Gln Thr Thr Glu Val
785                 790                 795                 800

Pro Val Gly Ala Leu Gly Ile Ala Val Ser
                805                 810

<210> SEQ ID NO 8
<211> LENGTH: 808
<212> TYPE: PRT
<213> ORGANISM: Bos taurus

<400> SEQUENCE: 8

Met Gly Arg Leu Leu Ser Val Leu Met Phe Pro Val Ser Cys Leu Ile
1               5                   10                  15

Leu Leu Trp Val Ala Gly Ser Gly Ser Met Arg Val Leu Gln Asp Pro
            20                  25                  30

Thr Cys Phe Ser Asp Tyr Ile Ser Asn Ser Thr Cys Glu Trp Glu Met
        35                  40                  45

Ala Gly Pro Thr Asn Cys Arg Ala Glu Leu His Leu Ser Tyr Gln Leu
    50                  55                  60

Asp Phe Tyr Tyr Ser Glu Asn His Thr Cys Val Pro Glu Asn Arg Ala
65                  70                  75                  80

Gly Val Gly Gly Thr Val Lys Ile Cys His Met Leu Thr Glu Asp Pro
                85                  90                  95

Val Arg Gln Asp Ile Tyr Gln Leu Asp Leu Trp Ala Gly Lys Gln Leu
            100                 105                 110

Leu Trp Asp Ser Ser Phe Lys Pro Ser Glu His Val Lys Pro Pro Ala
        115                 120                 125

Pro Arg Asn Leu Thr Val His Ala Asp Ile Ser His Thr Trp Leu Leu
    130                 135                 140

Thr Trp Asn Asn Pro Tyr Pro Ser Asp Asn Leu Leu Tyr Ser Glu Leu
145                 150                 155                 160

Thr Tyr Leu Val Asp Ile Ser Asn Glu Asn Asp Pro Thr Asp Phe Arg
                165                 170                 175

Thr Tyr Asn Val Thr Tyr Met Gly Pro Thr Leu Arg Val Ala Ala Ser
            180                 185                 190

Thr Leu Arg Ser Gly Ala Ser Tyr Ser Ala Arg Val Lys Ala Trp Ala
        195                 200                 205

Gln Ser Tyr Asn Ser Ser Trp Ser Ala Trp Ser Pro Ser Thr Lys Trp
    210                 215                 220

Leu Asn Tyr Tyr Glu Asp Thr Trp Glu Gln Arg Leu Gln Leu Gly Val
225                 230                 235                 240

Gly Ile Ser Cys Val Ile Val Leu Ala Val Cys Val Ser Cys Tyr Ile
                245                 250                 255

Ser Ile Ile Lys Ile Lys Lys Glu Trp Trp Asp Gln Ile Pro Asp Pro
```

```
            260                 265                 270
Ala His Ser Pro Leu Val Ala Val Val Ile Gln Asp Ser Gln Val Ser
            275                 280                 285

Leu Trp Arg Lys Arg Ser Arg Gly Gln Glu Pro Ala Lys Cys Pro His
            290                 295                 300

Trp Lys Thr Cys Leu Ala Lys Leu Leu Pro Cys Leu Leu Glu His Gly
305                 310                 315                 320

Met Glu Arg Asp Asp Asp Phe Ser Lys Ala Ala Arg Asp Gly Pro Ser
                    325                 330                 335

Gln Gly Ser Gly Lys Val Ala Trp Cys Pro Val Glu Val Ser Lys Thr
            340                 345                 350

Ile Leu Arg Pro Glu Ser Ile Ser Val Val Arg Cys Val Glu Leu Phe
            355                 360                 365

Glu Ala Gln Val Glu Lys Glu Glu Glu Val Glu Glu Asp Lys Gly
            370                 375                 380

Ser Phe Cys Pro Ser Pro Glu Asp Ser Gly Gly Leu Phe Gln Glu Gly
385                 390                 395                 400

Arg Glu Asp Ile Ala Ala Arg Leu Thr Glu Ser Leu Phe Leu His Leu
                    405                 410                 415

Leu Arg Asp Glu Thr Gly Gly Pro Ser Pro Gln Gly Val Glu Ser Cys
            420                 425                 430

Leu Leu Pro Pro Leu Glu Asn Ala Asn Ala Gln Arg Pro Trp Ala Glu
            435                 440                 445

Phe Pro Arg Val Glu Pro Gln Glu Ala Ser Ser Glu Asp Lys Glu Gln
            450                 455                 460

Pro Leu Ser Pro Glu Ser Ser Pro Gly Thr Pro Thr Gln Asn Pro
465                 470                 475                 480

Ala Gly Leu Pro Leu Pro Glu Met Pro Thr Ile Ile Ser Asp Asn Pro
                    485                 490                 495

Ala Tyr Arg Ser Phe Ser Thr Phe Leu Ser Gln Ser Ser Gly Pro Gly
            500                 505                 510

Glu Leu Asp Ser Asp Pro Gln Leu Ala Glu Cys Leu Gly Glu Val Asp
            515                 520                 525

Pro Asn Ile Pro Thr Thr Pro Lys Pro Glu Pro Glu Thr Trp Glu Gln
530                 535                 540

Ile Leu Arg Gln Arg Val Leu Gln His Arg Ala Ala Pro Gly Pro Ala
545                 550                 555                 560

Ser Ala Pro Ser Ser Gly Tyr Arg Glu Phe Val Gln Ala Val Lys Glu
                    565                 570                 575

Gly Gly Thr Gln Asp Ser Gly Pro Ala Gly Phe Gly Pro Ser Glu Glu
            580                 585                 590

Ala Gly Tyr Lys Ala Pro Ser Ser Leu Leu Ala Ser Ser Asp Ser Cys
            595                 600                 605

Pro Ala Thr Ser Gly Val Asp Pro Ser Ser Gly Glu Gly Gly Tyr Lys
            610                 615                 620

Pro Phe Gln Ser Leu Ala Ser Gly Cys Pro Arg Thr Pro Ser Pro Thr
625                 630                 635                 640

Pro Val Pro Leu Phe Thr Phe Gly Leu Asp Met Asp Pro His Ser
                    645                 650                 655

Pro Gln Asp Ser Glu Trp Pro Glu Leu Glu Pro Ala Val Lys Gly Asp
            660                 665                 670

Asp Gly Gln Lys Pro Leu Phe Ala Pro Val Pro Val Thr Asp Pro Leu
            675                 680                 685
```

```
Arg Asp Asp Leu Gly Asn Gly Ile Ile Tyr Ser Ala Leu Thr Cys His
    690             695                 700

Leu Cys Gly His Leu Lys Gln Cys His Gly Gln Glu Glu Ala Gly Lys
705                 710                 715                 720

Ala Gln Ile Val Val Ser Pro Cys Cys Gly Cys Cys Cys Gly Asp Arg
                725                 730                 735

Ser Ser Pro Leu Leu Ser Pro Leu Lys Ala Pro Asp Ser Leu Pro Gln
            740                 745                 750

Gly Thr Pro Leu Ala Ala Ser Leu Ser Ala Ala Ser Leu Ala Pro Leu
            755                 760                 765

Gly Val Ser Glu Glu Gly Lys Cys Pro Leu Phe Asn Ala Pro Ser His
770                 775                 780

Ala Gln Ser Ser Gly Gln Ala Pro Ala Val Thr Ala Val Pro Ser Pro
785                 790                 795                 800

Gly Pro Thr Cys Met Asp Ala Ser
                805
```

<210> SEQ ID NO 9
<211> LENGTH: 3251
<212> TYPE: DNA
<213> ORGANISM: Macaca mulatta

<400> SEQUENCE: 9

| | |
|---|---|
| ccggccaggg cagggccgcc caggggtccc ccacttcccg ctcggcgcc cggacggcga | 60 |
| atggagcagg ggcgcgcagg tgccttggca tctcccaatg gggtggcttt gctctgggct | 120 |
| cctgttccct gtgagctgcc tggtcctgct gcaggtggca agctctggga gcatgaaggt | 180 |
| cctgcaggag cccgcctgcg tctctgacta catgagcatc tctacctgtg agtggaagat | 240 |
| gggcggtccc accaattgca gcgccgagct ccgtctgttg taccagctgg tttttcagtc | 300 |
| ctccgaaacc cacacgtgtg tccccgagaa caacggcggt gtggggtgcg tgtgccacct | 360 |
| gctcatggat gatgtggtca gtatggacaa ctatacgctg gacctgtggg ctggacagca | 420 |
| gctgctgtgg aagggctcct tcaagcccag cgagcatgtg aaacccaggg ccccaggaaa | 480 |
| cctcacggtt cacaccaatg tctccgacac tgtgctgctg acctggagca acccgtatcc | 540 |
| ccctgacaat tacctgtata atgatctcac ctatgcagtc aacatttgga gtgaaaacga | 600 |
| cccggcatat tccagaatcc ataacgtgac ctacctaaaa cccaccctcc gcatcccagc | 660 |
| cagcacccctg aagtctggaa tttcctacag ggcacgggtg agggcctggg ctcagcacta | 720 |
| taacaccacc tggagtgagt ggagcccag caccaagtgg tacaactcct acagggagcc | 780 |
| cttcgagcag cgcctcctgt ggggtgtcag cgccgcctgc gttttcatcc tgttcttctg | 840 |
| cctgtcgtgc tatttcagcg tcaccaagat taagaaagaa tggtgggacc agattcccaa | 900 |
| cccagcccgc agccacctcg tggctataat aatccaggat gctcaggagt cacagtggga | 960 |
| gaagcgatcc cgaggccagg aagcagccaa atgcccatac tggaagaatt gtcttaccaa | 1020 |
| gctcttgccc tgttttctgg agcacaacat gaaaagggat gaggatcccc acaaggctgt | 1080 |
| caaagatctg ccattccggg ctctggaaa atcagcatgg tgccggtgg agatcagcaa | 1140 |
| gacagtcctc tggccagaga gcatcagcgt ggtgcgatgc gtggagttgt tgaggctcc | 1200 |
| agtggagtgt aaggaggagg aggaggtaga ggaagaaaaa gggagcttct gtacatcatc | 1260 |
| tgagagcaat agggatgact tccaggaggg aagggagggt attgtggccc ggctaacaga | 1320 |
| gagcctgttc ctggacctgc tcggagggga gaatgggggc ttttccagc aggacatggg | 1380 |
| ggagtcgtgc cttcttccac ctttgggaag cacgagtgct cacgtgccct gggatgagtt | 1440 |

| | |
|---|---|
| cccaagtgcc gggcccaagg aggtgcctcc ctggggcaag gagcagcctc tccaccagga | 1500 |
| gccgagtcct cctgccagcc caacgcagag cccagacaac ccgacttgca cagagatgcc | 1560 |
| cctcgtcatc tcaagcaacc ctgcttaccg tagcttcagc aactccctga gccagtcccc | 1620 |
| atgtcccaga gagctgggtc cagacccgct gctggccaga catctggagg aatgtggatt | 1680 |
| tggggctagc agtggggaag aggggtataa gcctttccaa gacctcactc ctggctgccc | 1740 |
| cggggaccct gccccagtcc ctgtccccttt gttcacctttt ggactggaca gggagccacc | 1800 |
| tcacagccca cagagctcac acctcccaag caactcccca gagcacctgg ctctggaacc | 1860 |
| aggggaaaaa gtagaggaca tgcaaaagcc cccactcccc ccggagcagg ccacagaccc | 1920 |
| ccttggggac aacctgggca gtggcatcgt ctactcagcc ctcacctgcc acctgtgcgg | 1980 |
| ccacctgaag cagtgtcatg gccaggagga tggtggccag gcccctgtcg tggccagtcc | 2040 |
| ctgctgtggc tgctgctgtg gagacaggtc ctcgcccct acaaccccc tgagggcccc | 2100 |
| agacccctct ctaggtgggg ttccactgga ggccagcctc tgtccggcct ccctggcacc | 2160 |
| ctcgggcatc tcagagaaga gtaaatcctc actgtccttc catcctgccc ctggcagtgc | 2220 |
| tcagagctca agccagactc cccagatcgt gaactttgtc tccgtgggtc ccacatgcat | 2280 |
| gagggtctct taggtgcgtg ccgtcttgtt gctgaggtct gcagataagg actagggctt | 2340 |
| atccatgcct gggaaatgcc acctcttgga aggcagccag gctggcagat ttccaaaaga | 2400 |
| cttgaagaaa tgtggtatga aggtgttagg ttccactgac attggcctaa cgctgggttg | 2460 |
| cagagactgg actctgccca gcattgggct gggctcgcca catccaatga gggagaggg | 2520 |
| cactgggtcg ctgtgcccca cggcaggccc ctgcaggaaa actgacatcc ttgggcacct | 2580 |
| cgacttgtga acaagttgtt ggctgctcca tccacaactt ctgtagcaga ctgtccctgt | 2640 |
| tgtacctgcc cagggcatgt tttgcccgcc aaatcaccat ggcccacata gaggcccacc | 2700 |
| tgcctctgtc tcactgaact agaagctgag cctagaaact aacacagtca tcaagggaat | 2760 |
| gacttgggcg gccttgggaa atcgatgaga aattgcagtt cagggaaggt ggtcattgcc | 2820 |
| tagaggtgct cttcattga acagagcttc cttaggttga tgctggaggc aggatcccgg | 2880 |
| ctgtcaaggg gtgttcagtt aaggggagca gcagaggaca tgaaaaattg cgatgactag | 2940 |
| agcagggaca atttgctgcc aaataccat gcacagctgt atggctgggg gctcctcgca | 3000 |
| tgcttgggac cccagaatg aatatgctca gctaccctgt ggggccgagca atccaggcag | 3060 |
| caggcataag gcaccggtta ccctgcacgt tggcccagac ctcaggtgct agggaaggcg | 3120 |
| gggaccttgg cttgagtaat gctcatctgt gtgttttaaa gatagtttca tcacctgttg | 3180 |
| tctgtgtttg ctgaggagag tggaacagaa ggggtggagt tttgtataaa taaagtttct | 3240 |
| ttgtctctttt a | 3251 |

<210> SEQ ID NO 10
<211> LENGTH: 3521
<212> TYPE: DNA
<213> ORGANISM: Bos taurus

<400> SEQUENCE: 10

| | |
|---|---|
| cgcggcgaat ggacctggag cgcgcaggca ccgtaggatc tcccgatggg gcggcttctc | 60 |
| tctgtactca tgttcccagt gagctgcctg atcctgttat gggtggccgg ctctgggagc | 120 |
| atgagggtcc ttcaggatcc cacctgcttc tcggactaca tcagcaactc cacctgtgag | 180 |
| tgggagatgg ccggacccac caactgcaga gccgagctgc acctgtccta ccagctgaat | 240 |
| ttttactact ctgaaaacca cacatgtgtc cccgagaaca gagcaggtgt gggggcaca | 300 |

```
gtgtgcatat gccatatgct gacagagaac ccagtcagac aagacatcta ccagctggac      360
ctgtgggcag ggaagcagct actgtggaac agctccttca agcccagcga gcacgtgaaa      420
ccaccggccc ccagaaacct cacggttcac gccgacatct cccacacgtg gctgctgacg      480
tggaacaacc cgtacccttc tgataacctc ctgtactccg agctcaccta cctggtcaac      540
atctcaaatg aaaatgaccc cacggatttc agaacctata acgtgaccta catggggccc      600
accctgcgtg tcgcggccag caccctgagg tctggagctt cctacagcgc acgggtgaag      660
gcctgggctc agagctacaa cagcagctgg agcgcgtgga gccccagcac caagtggctt      720
aactactacg aggacacctg ggagcagcgc ctccagctgg gcgtcggcat ctcgtgcgtc      780
atcgtcctgg cggtgtgcgt gtcctgctac atcagcatca tcaagattaa gaaagaatgg      840
tgggaccaaa ttcccaaccc agcccacagc ccccttgtgg ctgttgtcat ccaggattct      900
caggtgtcac tgtggaggaa gcggtctcga ggccaggaac cagccaaatg cccacactgg      960
aagacttgtc ttgccaagct cctgcccgt ttactggagc atggcatgga gagggatgac     1020
gacttctcta aggctgctag aaatgggcct tcccagggtt ctgggaaagt agcatggtgc     1080
cccgtggagg tcagcaagac gatcctccgg cctgagagca tcagcgtggt gcggtgcgtg     1140
gagctgtttg aggcccaagt ggagaaggaa gaagaggaag tggaggaaga taaagggagc     1200
ttctgcccat cacctgagaa cagcgggggc ctcttccagg agggcagaga ggacattgcg     1260
gcccggctga cagagagcct gttcctgcac cttctcagag atgagactgg gggctttagt     1320
ccacaaggtg tggagtcctg ccttcttccc cctttagaaa atgcaaatgc tcagaggccc     1380
tgggccgaat tcccaagggt ggagccccag gaggcatcat ctgaggacaa ggaacagcct     1440
ctgagcccag agtcaagtcc tccgggcact ccaacccaga acccagccgg cctgcctctc     1500
ccagagatgc ccaccatcat ctcagacaac cctgcttacc gcagcttcag caccttcctg     1560
agccagtcct cgggcctgg agagcttgac tcagacccac agctggccga atgcctgggg     1620
gaagtggacc ccaacatccc caccaccccc aagccggaac cagagacctg ggaacagatt     1680
ctgcgtcaga gggtgctcca gcacagggcg gcccccggcc ccgcctcggc ccctagcagc     1740
ggctaccggg aatttgtgca ggcggtgaag gagggtggca cccaggacag cgggccggct     1800
ggctttgggc cctctgaaga ggccggctac aaggccttct ccagcttgct tgccagcagt     1860
gacagctgcc ctgcgacttc tggggttgac cccagcagcg ggaagggggg ctacaaaccc     1920
ttccagagcc ttgcttctgg ctgccccagg accccttccc ccactcccgt tccctgttc      1980 actttcggcc tggacatgga ccccccctca agtcctcagg actcagagtg gcctgagttg     2040
gagccagcag tcaagggaga cgatggacag aaaccctct tcgccccgt gccggtcaca      2100 gaccctctca gggacgacct gggcaacggc atcatctact cagccctcac ctgccaccta     2160
tgtggccacc tgaagcagtg ccacggccag gaggaagctg gcaaggcgca aattgtggtc     2220
agcccctgct gcggttgctg ctgtgggac aggtcctcgc ctctgctgag tccgctgaaa      2280
gccccagact ccctgcccca ggggactcca ctggcagcca gcctctctgc ggcctcccta     2340
gcacccttag gtgtctcaga ggagggtaag tgccctctgt tcaatgcccc cagccatgcc     2400
cagagctcag gccaggctcc tgcagtgact gccgtgccct cccaggccc cacgtgcatg     2460 gacgcttcct aggtgcgtgc ccgctccttg ctgaagtcta cagaggagat ggggccttaa     2520
tcaggcctgt gaaatgcctg cccctggaag gccgccaggc tggcagagtt ccagaagact     2580
ctgggaactc tggagtgaag ttctcagacg ccaggtctac agggactgga cgcccccagc     2640 tcccttgct ggccccggct caccacctcc cacgggagtg ggggctccag gcagctgtgc      2700
```

```
ccacagaggc acctgcagtc atctggagat gccccgggca ccttggcttg tgcaccttgg  2760
ccacttcact ggttcacaga tgtgccagca gactgtccct ggcatactca aggcatattc  2820
tgtcactctg acccagttct tgcccagact ccggagtagc taccaccatc tctctagatt  2880
ggatgctgag cctagaaact caccaagcca actggggaat tgacttggga ggccttggga  2940
aattgaggtc caggaagggt ggtaatctgc ccagagatgt ctattcattc aacagaagtt  3000
gacgctgggg gcaaggtctg agctgcagag gggtgattaa ttaagtggag ttaaccaagg  3060
acatgataaa ttgtgatttc tgagacgtga cagcttgtgg ccagcttccc acgcaaggct  3120
gggattcctg ttaagcattg gatccccaga gaagaggcat gcctggcaac cttggggcag  3180
gcgtgtgccc ccagggatgc cattgctggc atcactgctt cagaaggtgt ggctcaggcc  3240
ccctgatcca gtgagctggg gcgaccaaga cgctgacacc aggcacatca cccacacatc  3300
atcaactccc acctcaggtt gaagaatgct tgtttgtgtg catctcaaaa attatttcat  3360
cactgggtgt ttgtgtttgc tgaggagggt ggaatgggaa gagatggagt tttgtataaa  3420
taaaggttct ttatctcttt cccctccccc gccaccattt attaaacaaa catcctgcca  3480
agcaaaaaaa aaaaaaaaaa aaaaaaaaaa aaaaaaaaa a                       3521
```

ANTISENSE RESPIRATORY SYNCYTIAL VIRUS VACCINE AND THERAPY

CROSS-REFERENCE TO RELATED APPLICATIONS

The present application claims the benefit of prior U.S. Provisional Application No. 60/983,040, filed Oct. 26, 2007.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

The Sequence Listing, which is a part of the present disclosure and is submitted in conformity with 37 CFR §§1.821-1.825, includes a computer readable form and a written sequence listing comprising nucleotide and/or amino acid sequences of the present invention. The sequence listing information recorded in computer readable form (created 22 Oct. 2007; filename: RSV_vaccine_ST25; size: 45.4 KB) is identical to the written sequence listing below. The subject matter of the Sequence Listing is incorporated herein by reference in its entirety.

BACKGROUND OF THE INVENTION

1. Field of the Invention

The present invention relates to polynucleotide molecules (e.g., DNA, RNA, etc.). More particularly, the invention relates to antisense oligonucleotides useful for prevention, amelioration, and treatment of wheeze and other diseases related to pulmonary inflammation, pulmonary dysfunction, and airway hyperresponsiveness. In particular, the invention relates to antisense oligonucleotides useful for suppressing IL-4Rα-mediated signaling during a critical developmental period, thereby preventing, ameliorating, and treating RSV-associated airway diseases.

2. Description of Related Art

Asthma is epidemic among industrialized countries (Cookson W O & Moffatt M F, *Science* 1997; 275:41-42). Although molecular analyses have suggested a genetic basis for this disease state (se e.g., Daniels S E, et al. *Nature* 1996; 383:247-50; Van Eerdewegh P, et al. *Nature* 2002; 418:426-30), environmental factors are partly responsible. Hypotheses for the proliferation of asthma have focused on exacerbating factors such as air pollution (McBride D E, et al. *Am J Respir Crit Care Med.* 1994; 149:1192-97), early exposure to "trigger" antigens (e.g., dust mites, cockroaches) (O'Byrne P M. *J Allergy Clin Immunol.* 1988; 81:119-27), tobacco/chemical exposure (Flodin U, et al. *Epidemiology* 1995; 6:503-505), and increased amount of time spent outdoors versus indoors (Platts-Mills T A, et al. *Curr Opin Immunol.* 1998; 10:634-39). Moreover, the increased incidence of respiratory infections (e.g., respiratory syncytial virus (RSV), rhinovirus, and parainfluenza) associated with greater numbers of people living in high-density urban environments has also been proposed as a predisposing factor in the rising prevalence of asthma (Wang S Z & Forsyth K D. *Clin Exper Allergy.* 1998; 28:927-35). Despite intense study of patient populations, the unique circumstances that dictate why one person's immune responses lead to asthma when others' do not are still obscure.

Asthma is a respiratory disorder characterized by recurring episodes of paroxysmal dyspnea (sudden shortness of breath), wheezing on expiration due to constriction of bronchi, coughing, and viscous mucoid bronchial secretions (Mosby's Medical and Nursing Dictionary, 1990). Wheeze is a form of rhonchus (abnormal sounds heard upon auscultation of a respiratory airway obstructed by, e.g., thick secretions), characterized by a high-pitched musical quality and caused by a high-velocity flow of air through a narrowed airway (Id). Wheezes may be heard both during inspiration and expiration, and are associated with asthma, chronic bronchitis, chronic obstructive pulmonary disease (COPD), pulmonary edema, and respiratory infections, among other things. Although the etiology and symptoms of asthma are highly variable among patients, three common characteristic features of asthma exist: reversible variable airflow limitations; specific airway histopathologies due to airway inflammation and damage; and airway hyperresponsiveness (AHR, the development of bronchoconstriction in response to non-specific inflammatory stimuli) (Bochner B S, et al. *Annu Rev Immunol.* 1994; 12:295-35). The onset and progression of allergic asthma is accompanied by a complex series of overlapping and concurrent inflammatory responses in the lung orchestrated by CD4+ Th2 lymphocytes (Type 2 T helper cells expressing CD4+). (Gavett S H, et al. *Am J Respir Cell Mol Biol.* 1994; 10:587-93. Kon O M & Kay A B. *Int Arch Allergy Immunol.* 1999; 118:133-35. Robinson D, et al. *J Allergy Clin Immunol.* 1993; 92:313-24. Walker C, et al. *Am Rev Respir Dis.* 1992; 146(1):109-15. Kay A B. *Ciba Found Symp.* 1997; 206:56-67.) These responses include T cell mediated help of antigen-specific immunoglobulin production particularly IgG1 and IgE by B cells (DeKruyff R H, et al. *Semin Immunol.* 1993; 5:421-30. Jenmalm M C, et al. *Pediatr Allergy Immunol.* 1999; 10:168-77.), expression of Th2 proinflammatory cytokines (e.g. IL-4, -5, -9, and -13) (Hoppler S & Bienz M. *Cell.* 1994; 76:689-702. Host A H, et al. Ugeskr Laeger [Danish]. 1993; 155:3978-81. Till S, et al. *Immunology* 1997; 9153-57.), and the activation of stromal and epithelial cells leading to the release of chemokines that initiate and perpetuate lung inflammatory reactions (Levine S J. *J Investig Med.* 1995; 43:241-49.). Asthma-associated pulmonary inflammation is also characterized by cellular infiltrates, which are believed to be involved subsequently in histopathologies and are also thought to be the underlying cause(s) of the accompanying airway obstruction and lung dysfunction.

For many years, it was thought that "reversible" airflow obstruction meant that asthma was also reversible. Thus, it was anticipated that childhood asthma was a self-limiting disorder that the child would "outgrow." However, recent evidence suggests that repeated injury to the lung results in structural airway changes that—under some conditions—are irreversible. It is now well recognized that the majority of children with moderate to severe symptoms continue to wheeze and have reduced lung function values as adults. Even though they may consider themselves "symptom-free," they continue to show reduced lung function and increased bronchial reactivity to both specific and non-specific stimuli (Pedersen S, "Asthma in Children," In: *Asthma Basic Mechanisms and Clinical Management* (Peter J. Barnes, Ian W. Rodger, and Neil C Thompson, eds., Academic Press 1998), 3d ed., pp. 859-902.). The exact reason(s) for the long-term decline in lung function is uncertain, but pulmonary remodeling is a likely explanation. Supporting evidence comes from a study in which rats were repeatedly exposed to aerosolized ovalbumin (OVA) (Palmans E, et al. *Am J Respir Crit Care Med.* 2000; 161:627-35.). This resulted in AHR to carbachol, which was accompanied by structural changes/remodeling of the airways, including goblet cell hyperplasia, increased proliferation of airway epithelium, increased deposition of fibronectin, and increased thickness of the interstitial matrix (Palmans E, 2000).

Interestingly, human studies have demonstrated that airway remodeling events associated with asthma begin early in life, and in some infants are observable at the pathological level prior to the clinical onset of asthma symptoms (Warner J A. *J Allergy Clin Immunol.* 2000; 105:951-59. Group TCAMPR. *N Engl J Med.* 2000:343; 1054-63.). The immature lung is saccular (sack-like) in structure, and has a limited gas-exchange capability. Maturation into a mature lung with a large internal surface area capable of highly efficient gas exchange requires thinning of the alveolar walls, extensive subdivision of saccular lung into alveoli, and growth of the pulmonary capillary network (Ad hoc Statement Committee, American Thoracic Society. *Am J Respir Crit Care Med.* 2004; 170:319-43.). In humans, this maturation process begins at 36 weeks of gestation. Only 15% of the alveoli have formed at birth, and maturation continues into the third year of life (Dunnill M. *Thorax.* 1962; 17:329-33. Burn P, "Structural aspects of prenatal and postnatal development and growth of the lung," In: *Lung Growth and Development* (John A. McDonald ed., Informa Healthcare 1997), 1st ed., pp. 1-35. Merkus P, et al. *Pediatric Pulmonology.* 1996; 21:383-97. Meyrick B & Reid L, "Ultrastructure of alveolar lining and its development," In: *Development of the Lung: Lung Biology in Health and Disease Series* (W. A Hodson ed., Marcel Dekker 1977), pp. 135-214.). Rodents are also born with the lung in saccular stage, with alveolarization and wall thinning occurring postnatally. At birth, the immature murine lung lacks alveoli, alveolar ducts, and respiratory bronchioles. Alveolarization in the rat occurs on portpartum days 4-7, and respiratory bronchioles are found 10 days after birth (Burn P. *Anat Rec.* 1974; 180:77-98.). Interestingly, increased oxidative stress due to mechanical lung ventilation in preterm human infants causes extensive alveolar fibroproliferation, smooth muscle hyperplasia, and inhibition of distal lung formation, and also leads to long-term pulmonary dysfunction persisting into adulthood (Northway W, et al. *N Engl J Med.* 1967; 276:357-68. Kurzner S I, et al. *J. Pediatr.* 1988; 112:73-80.). These data suggest that infant lung tissue responds to external environmental factors that can influence pulmonary patterning, extent of lung growth, and long-term physiologic function.

Three broad influences are currently believed to be the most important factors in the development of asthma: genetics; environmental factors (i.e., exposure to allergens or pathogens); and interactions between these factors and the developing immune/pulmonary system in early life. As a fetus, and shortly after birth, the immune system is prone to Th2 responses (Adkins B. *Int Rev Immunol.* 2000; 19(2-3):157-71.). In the fetus this Th2 bias is thought to protect both the mother from cytotoxic Th1 (Type 1 T helper cell) fetal responses and the fetus from maternal rejection (Wegmann T G, et al. *Immunol Today.* 1993; 14:353-56.). After birth, the immune system begins to mature in an age- and exposure-dependent manner. In humans, the Th2 cytokine profile persists throughout the first year of life and is accompanied by a relative eosinophilia (Prescott S L, et al. *Lancet.* 1999; 353:196-200. Bruce M. Camitta, "The anemias," In: *Nelson Textbook of Pediatrics* (Ricard E. Behrman, Robert M. Kliegman, and Ann M. Arvin, eds., W.B. Saunders 1996) 15th ed., pp. 1379.). In mice, the Th2 cytokine profile persists until approximately three weeks of age (Becnel D, et al. *Respir Res.* 2005; 6:122. You D, et al. *Respir Res.* 2006; 7:107.).

One particular environmental factor—respiratory syncytial virus (RSV), a member of a subgroup of myxoviruses—is the most common cause of bronchiolitis (acute viral infection of the lower respiratory tract) and pneumonia (acute inflammation of the lungs) in humans during infancy. Usually, symptoms begin with fever, runny nose, cough, and sometimes wheezing. During their first RSV infection, approximately 25% to 40% of human infants present signs of bronchiolitis or pneumonia, and they usually recover within 8 to 15 days. Approximately 0.5% to 2% of RSV-infected children require hospitalization, and the majority of these are under 6 months of age. Most human children have serologic evidence of RSV infection by 2 years of age (Glezen W P, et al. *Am J Dis Child.* 1986; 140:543-6.). RSV may cause repeated infections throughout one's life, with community-wide infections usually occurring in late fall, winter, or early spring months. A diagnosis of RSV infection may be made by detection of viral antigens, viral mRNA, or a rise in serum antibodies, by isolation of the virus, or by a combination of these strategies. Most commonly, antigen detection assays are employed. Moreover, infections of cattle and goats with bovine RSV and of sheep with ovine RSV are widespread, and produce significant economic losses (Mallipeddi S K & Samal S K. *J Gen Vir.* 1993; 74:2787-91.). Although the development of vaccines against RSV is a pressing research priority, they are either unavailable or present serious drawbacks.

Several retrospective and prospective human studies have suggested a link between RSV lower respiratory tract infections during infancy and later development of asthma (Sims D G, et al. *Br Med J.* 1978; 1:11-14. Pullan C R & Hey E N. *Br Med J (Clin Res Ed).* 1982; 284:1665-69. McConnochie K M & Roghmann K J. Pediatrics. 1984; 74:1-10. Mok J Y & Simpson H. *Arch Dis Child.* 1984; 59:306-9. Murray M, et al. *Arch Dis Child* 1992; 67:482-7. Noble V, et al. *Arch Dis Child.* 1997; 76:315-9. Stein R T, et al. *Lancet.* 1999; 354:541-5. Sigurs N, et al. *Am J Respir Crit Care Med* 2005; 171:137-41. Piippo-Savolainen E, et al. *Allegy Asthma Proc.* 2007; 28:163-69. Openshaw P M J. *Clin Exp Immunol.* 2003; 131:197-198.). Two ongoing longitudinal studies clearly demonstrate that RSV in early life does increase the risk of wheeze (and perhaps asthma) in later childhood (Stein R T, et al., 1999. Sigurs N, et al., 2005.).

In one study, 43% of children diagnosed with severe RSV bronchiolitis as infants still experienced asthma or wheeze at 13 years of age, compared to only 8% of control patients (Sigurs N, et al., 2005.). Interestingly, 50% of children who had RSV bronchiolitis also tested positive to aeroallergens, versus 28% of controls (Id.). These results suggest that severe RSV infection during infancy predisposes one not only to the development of asthma or wheeze, but also to the development of allergic disease (Id). Multivariant analysis demonstrated that the highest frequency of wheeze was observed when RSV bronchiolitis and a family history of atopy were present as risk factors (68% of the RSV group as compared to 34% of the control group) (Id). Results obtained from the Tucson Children's Respiratory Study found that children with even mild RSV infections were four times more likely to have recurrent, frequent wheeze by 6 years of age (Stein R T, et al., 1999.). By 13 years of age, though, the association between wheeze and RSV was no longer significant. This study also showed no relationship between RSV infection and positive skin reactivity tests to aeroallergens (Id). Some factors that may account for the lack of consistency between the prospective studies on the relationship between RSV and the development of asthma are: (i) recruitment of infants (only the sickest infants hospitalized); (ii) inaccuracy of RSV testing, which often requires multiple tests to achieve a positive result; (iii) reliance on parental answers to judge continued wheeze, as with the Tucson Study, (iv) differences in gestational ages of the children recruited; and (v) differences between RSV strains, which may produce different immunological and physiological responses. Cumulatively, the data suggest that RSV bronchiolitis in infancy is associated with an increased risk of wheeze, which may persist for several years and is not adequately explained by allergies or a family history of atopy.

Previous efforts at creating a human vaccine against RSV produced tragic consequences. In the mid-1960s, an experimental formalin-inactived RSV vaccine was developed and administered parenterally to infants between two and seven months of age (Kim H W, et al. *Am J Epidemiol.* 1969; 89:422-434.). The vaccine caused a measurable serum-neutralizing antibody response, but when RSV became prevalent in the community (i.e., when those vaccinated were later infected naturally) 80% of those vaccinated required hospitalization for pneumonia and/or bronchiolitis. Two infants died (Id.). Post-mortem examinations revealed pneumonia and patchy atelectasis, while histologic analysis revealed peribronchiolar eosinophilia (Id.). Further studies in adult mice using formalin-inactivated RSV confirmed the above findings (Power U F, et al. *J. Virol.* 2001; 75:12421-30. Peebles R S Jr., et al. *J Infect Dis.* 2000; 182:671-77.). Numerous subsequent studies have demonstrated that RSV infection enhances Th2 cytokine responses and eosinophilic infiltration following allergen sensitization and challenge (Becnel D, et al., 2005. You D, et al., 2006. Barends M, et al. *Clin Exp Allergy.* 2002; 32:463-71. Peebles R S Jr., et al. *J Med Virol.* 1999; 57:186-92.).

A recent study by Culley, et al. presented the first evidence demonstrating that "infections in early life play an important role" in shaping the secondary response to antigen, and can lead to long-term consequences for the host (Culley F J, et al. *J Exp Med.* 2002; 196:1381-86.). Culley, et al. demonstrated that the age of initial infection with RSV played a significant role in the secondary response to rechallenge with RSV. As seen in FIG. 1, the immune response of mice initially infected with RSV between 1 and 7 days of age and rechallenged at 12 weeks of age was characterized by increased bronchoalveolar lavage (BAL) cellularity, including increased eosinophil and neutrophil cell numbers, and increased CD8+ and CD4+ T cell production of intracellular interleukin 4 (IL-4) (FIG. 1). In contrast, the immune response of mice initially infected at 4 weeks of age and rechallenged at 12 weeks of age was characterized by decreased eosinophil and neutrophil cell numbers, decreased CD4+ T cell production of intracellular IL-4, and increased CD4+ T cell production of intracellular interferon gamma (IFN-γ) (FIG. 1). The work of Culley et al. suggests that the pattern of inflammatory cell response in infants may be important during re-infection but does not suggest how pulmonary dysfunction or RSV-related asthma later in life may be prevented.

The development of Th2 immune response is critically affected by IL-4 and IL-13 (FIG. 3). IL-4 is critical for the commitment of T helper cells to the Th2 lineage (relative to ml) and for IgE isotype switching, while IL-13 plays a critical role in the pathogenesis of allergic diseases including the development of AHR, lung remodeling, and mucus hyperproduction. IL-4 is a ligand for both the IL-4 type I (IL-4Rα and IL-4Rγc) and type II (IL-4Rα and IL-13Rα1) receptor heterodimers, and IL-13 exerts its actions by binding to the type II IL-4R (FIG. 3). IL-4Rα (see, e.g., SEQ ID NO:1, *H. sapi-ens* IL-4Rα, Accession No. NM_000418.2) is a high-affinity receptor for IL-4, and binding of IL-4 to this receptor promotes heterodimerization with a second chain (e.g., IL-4Rγc). Heterodimerization of IL-4R, in turn, activates down-stream signaling through members of the Janus kinase family, leading eventually to activation of signal transducer and activator of transcription (Stat6) protein and expression of various IL-4 inducible genes. Although a second IL-13 receptor (IL-13Rα2) exists, it is currently thought to be a non-signaling "decoy" receptor.

Recently, Karras, et al. demonstrated that reduction of IL-4Rα in the lungs (using inhaled antisense oligonucleotides against IL-4Rα) was sufficient to inhibit airway hyperresponsiveness and inflammation in an adult model of allergen-induced asthma (Karras J G, et al. *Am J Respir Cell Mol. Bid.* 2007; 36:276-85.). The findings of Karras, et al. support the use of inhaled IL-4Rα antisense oligonucleotides as a therapy for preexisting asthma and asthma exacerbations by essentially blocking Th2 effector cell function. In contrast, the present invention focuses on the use of IL-4R antisense oligonucleotides in the blocking the initiation of Th2 cellular differentiation and effector function in response to infant RSV infection, thereby inhibiting the pathophysiologic sequelae (e.g. persistent airway dysfunction and Th2 inflammatory responses upon subsequent exposure to RSV) that it initiates.

The technical problem underlying the present invention was therefore to overcome these prior art difficulties by inhibiting IL-4Rα in infants around the time that the T helper cell response is being influenced by RSV infection to develop as a Th2 response. The solution to this technical problem is provided by the embodiments characterized in the claims.

BRIEF SUMMARY OF THE INVENTION

The present invention provides methods of immunizing against RSV-induced pulmonary inflammation and airway hyperresponsiveness by administering at least one antisense oligonucleotide (ASO) to a subject in need thereof, wherein the subject is an infant and said infant is infected with a respiratory syncytial virus, the ASO is between 10 and 40 nucleotides in length, the ASO is targeted to a nucleic acid molecule encoding IL-4Rα, the first 5 and last 5 nucleotides at the 5' and 3' ends of the ASO are 2'-O-methoxyethyl nucleotides, the nucleotides between the first 5 and last 5 nucleotides at the 5' and 3' ends are 2'-deoxynucleotides, every internucleoside linkage is a phosphorothioate linkage, and every cytidine residue is a 5-methylcytidine. It is preferred that the ASO be single-stranded, and it is preferred that the route of ASO administration is inhalatory, and administration is most preferably to the nasal cavity and/or sinus. The ASO may be delivered using any kind of standard delivery device, including but not limited to nebulizers, inhalers (nasal and pulmonary), dry powder inhalers, and metered dose inhalers. When the subject in need thereof is a human, it is preferred that the subject is in the first year of life. It is also preferred, when the subject in need thereof is a human in the first year of life, that the ASO is targeted to nucleotides 167-265 of SEQ ID NO:1; the ASO may bear at least 75% sequence identity with the complement of nucleotides 167-265 of SEQ ID NO:1. It is also preferred, when the subject in need thereof is a human in the first year of life, that the ASO is targeted to nucleotides 357-515 of SEQ ID NO:1; the ASO may bear at least 75% sequence identity with the complement of nucleotides 357-515 of SEQ ID NO:1. When the subject in need thereof is a non-human primate, it is preferred that the subject is in the first 6 months of life. It is also preferred, when the subject in need thereof is a non-human primate in the first 6 months of life, that the ASO is targeted to nucleotides 89-154 of SEQ ID NO:9; the ASO may bear at least 75% sequence identity with the complement of nucleotides 89-154 of SEQ ID NO:9. It is also preferred, when the subject in need thereof is a non-human primate in the first 6 months of life, that the ASO is targeted to nucleotides 279-437 of SEQ ID NO:9; the ASO may bear at least 75% sequence identity with the complement of nucleotides 279-437 of SEQ ID NO:9. When the subject in need thereof is a bovine, it is preferred that the subject is in the first 8 weeks of life. It is also preferred, when the subject in need thereof is a bovine in the first 8 weeks of life, that the ASO is targeted to nucleotides 37-135 of SEQ ID NO:10; the ASO may bear at least 75% sequence identity with the complement of nucleotides 37-135 of SEQ ID NO:10. It is also preferred, when the subject in need thereof is a bovine in the first 8 weeks of life, that the ASO is targeted to nucleotides 227-385 of SEQ ID NO:10; the ASO may bear at least 75% sequence identity with the complement of nucleotides 227-385 of SEQ ID NO:10.

It is also an object of this invention to inhibit or suppress IL-4Rα expression using at least one antisense oligonucleotide sequence targeted to IL-4Rα to inhibit or substantially reduce the initiation of a Th2 immune response in infant RSV infection, thereby reducing the likelihood of later development of pulmonary inflammation and/or airway hyperresponsivenses. It is a further object of the invention to block signaling through IL-4Rα in an infant infected with RSV to allow for an increased Th1 immune response to infantile RSV infection initially and upon subsequent re-infection as an adult.

DEFINITIONS

The following definitions are provided to give a clear understanding of the specification and appended claims.

The acronym "ASO" as used herein means anti-sense oligonucleotide.

The acronym "dpi" as used herein means days post-infection.

The acronyms "MR" and "MM" as used herein mean mismatch antisense-oligonucleotide.

The acronym "$TCID_{50}$" as used herein means tissue culture infectious dose—the quantity of virus that will produce cytopathology in 50% of inoculated cultures.

As used herein, "airway resistance" means the opposition to motion of air caused by frictional forces, which is a function of airflow rate, airway caliber, and other variables. It is the ratio of pressure difference between the mouth, nose, or other airway opening and the alveoli to the simultaneously measured volumetric gas flow rate. In respiratory physiology, it describes mechanical factors that limit access of inspired air to pulmonary alveoli, and so determine airflow.

As used herein, "elastance" means the reciprocal of compliance. It is a measure of the change in pressure achieved per unit change in volume, or of stiffness. "Compliance" is the volume change per unit of pressure change across an elastic structure, such as a lung.

As used herein, "immunization" means a process by which resistance to RSV—or to the sequelae following and resulting from RSV infection, including but not limited to enhanced airway resistance, mucus hyperproduction, enhanced Th2 cytokine production, pulmonary inflammation, and airway hyperresponsivenses—is induced or augmented As used herein, "infant" as applied to human beings refers to a child in the two years of life; as applied to mice, "infant" refers to a mouse in the first twelve days of life; as applied to non-human primates, "infant" refers to an animal in the first 6 months of life; as applied to bovines, "infant" refers to an animal in the first 8 weeks of life; as applied to members of the genus *Ovis*, "infant" refers to an animal in the first 2 weeks of life; as applied to members of the genus *Capra*, "infant" refers to an animal in the first 2 weeks of life.

As used herein, the acronym "RSV" means "respiratory syncytial virus," which is an RNA virus that causes disease of the respiratory tract. When one is tainted with RSV disease or the infectious properties of RSV (e.g., when one's body has been invaded by RSV, or when one exhibits symptoms consistent with RSV illness), one is said to be "infected" with RSV or have an "RSV infection." "Infantile RSV infection" means RSV infection in an infant.

By "expression" or "gene expression" is meant transcription (e.g., from a gene) and, in some cases, translation of a gene into a protein, or "gene product" (e.g., cytokines). In the process of expression, a DNA chain coding for the sequence of gene product is first transcribed to a complementary RNA, which is often a messenger RNA, and, in some cases, the transcribed messenger RNA is then translated into the gene product—a protein. The terms are also used to mean the degree to which a gene is active in a cell or tissue, measured by the amount of mRNA in the tissue and/or the amount of protein expressed.

By "gene" is meant a nucleic acid (e.g., deoxyribonucleic acid, or "DNA") sequence that comprises coding sequences necessary for the production of a polypeptide or precursor (e.g., messenger RNA, or "mRNA"). The polypeptide may be encoded by a full length coding sequence or by any portion of the coding sequence, so long as the desired activity or functional properties (e.g., enzymatic activity, ligand binding, signal transduction, etc.) are retained. The term also encompasses the coding region of a structural gene and the sequences located adjacent to the coding region on both the 5' and 3' ends, for a distance of about 1 kb on either end, such that the gene is capable of being transcribed into a full-length mRNA. The sequences located 5' of the coding region and which are present on the mRNA are referred to as 5' untranslated sequences, and form the 5' untranslated region (5' UTR). The sequences located 3' or downstream of the coding region and which are present on the mRNA are referred to as 3' non-translated sequences, and form the 3' untranslated region (3' UTR). The term "gene" encompasses both cDNA and genomic forms of a gene. The genomic form or clone of a gene usually contains the coding region interrupted with non-coding sequences termed "introns" (also called "intervening regions" or "intervening sequences"). Introns are segments of a gene which are transcribed into nuclear RNA (hnRNA); introns may contain regulatory elements such as enhancers. Introns are removed or "spliced out" from the nuclear or primary transcript, and therefore are absent from the mRNA transcript. mRNA functions during translation to specify the sequence or order of amino acids in a nascent polypeptide.

By "nucleotide" is meant a monomeric structural unit of nucleic acid (e.g., DNA or RNA) consisting of a sugar moiety (a pentose: ribose, or deoxyribose), a phosphate group, and a nitrogenous heterocyclic base. The base is linked to the sugar moiety via a glycosidic bond (at the 1' carbon of the pentose ring) and the combination of base and sugar is called a nucleoside. When the nucleoside contains a phosphate group bonded to the 3' or 5' position of the pentose, it is referred to as a nucleotide. When the nucleotide contains one such phosphate group, it is referred to as a nucleotide monophosphate; with the addition of two or three such phosphate groups, it is called a nucleotide diphosphate or triphosphate, respectively. The most common, nucleotide bases are derivatives of purine or pyrimidine, with the most common purines being adenine and guanine, and the most common pyrimidines being thymidine, uracil, and cytosine. A sequence of operatively linked nucleotides is typically referred to herein as a "base sequence" or "nucleotide sequence" or "nucleic acid sequence," and is represented herein by a formula whose left-to-right orientation is in the conventional direction of 5'-terminus to 3'-terminus.

As used herein, the term "oligonucleotide," refers to a short length of single-stranded polynucleotide chain. Oligonucleotides are typically fewer than 100 residues long (e.g., between 15 and 50). Oligonucleotides are often referred to by their length. For example, a 24 residue oligonucleotide is referred to as a "24-mer". Oligonucleotides can form secondary and tertiary structures by self-hybridizing or by hybridizing to other polynucleotides (any polymer comprised of nucleotide monomers covalently bonded in a chain). Such structures can include, but are not limited to, duplexes, hairpins, cruciforms, bends, and triplexes. Nucleotides are the basic unit of DNA, and consist of a nitrogenous base (adenine, guanine, cytosine, or thymine), a phosphate molecule, and a deoxyribose molecule. When linked together, they form oligonucleotide molecules. "Antisense oligonucleotides," then, are single strands of RNA or DNA that are complementary to a particular RNA or DNA sequence. Antisense RNA oligonucleotides may prevent translation of complementary RNA strands by binding to them. Antisense DNA oligonucleotides may bind to complementary coding or non-coding RNA, thus targeting the DNA/RNA hybrid for degradation by the enzyme RNase H and so suppressing or preventing expression of the protein encoded by that RNA.

DNA molecules are said to have "5' ends" and "3' ends" because mononucleotides are joined to make oligonucleotides in a manner such that the 5' phosphate of one mononucleotide pentose ring is attached to the 3' oxygen of its neighbor in one direction, via a phosphodiester linkage. Therefore, an end of an oligonucleotide is referred to as the "5' end" if its 5'-phosphate is not linked to the 3' oxygen of a mononucleotide pentose ring. Alternatively, it is the "3' end" if its 3' oxygen is not linked to a 5' phosphate of a subsequent mononucleotide pentose ring. These ends are also referred to as "free" ends because they are not linked to upstream or downstream mononucleotides, respectively. A double stranded nucleic acid molecule may also be said to have 5'- and 3' ends, wherein the "5'" refers to the end containing the accepted beginning of the particular region, gene, or structure, and the "3'" refers to the end downstream of the 5' end. A nucleic acid sequence, even if internal to a larger oligonucleotide, may also be said to have 5' and 3' ends, although these ends are not free ends. In such a case, the 5' and 3' ends of the internal nucleic acid sequence refer to the 5' and 3' ends that said fragment would have were it isolated from the larger oligonucleotide.

By "protein" or "polypeptide" is meant a sequence of amino acids of any length, constituting all or a part of a naturally-occurring polypeptide or peptide, or constituting a non-naturally occurring polypeptide or peptide (e.g., a randomly generated peptide sequence or one of an intentionally designed collection of peptide sequences). A "test protein" or "test polypeptide" is a protein used according to the methods of the present invention to measure or test interaction between nucleic acids and said test protein or test polypeptide.

As used herein, the term "target" refers to an RNA sequence complementary to an oligonucleotide sequence. Thus, the "target" is bound by an oligonucleotide bearing a sequence complementary to the target.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

FIG. 12 shows the sequence comparison between IL-4Rα proteins of human (*Homo sapiens*, amino acids 27-121 of SEQ ID NO:5, Accession No. NM_000418.2), macaque (*Macaca mulatta*, amino acids 27-121 of SEQ ID NO:6), mouse (*Mus musculus*, amino acids 27-122 of SEQ ID NO:7, Accession No. NM_001008700.3), and bovine (*Bos taurus*, amino acids 27-124 of SEQ ID NO:8, Accession No. NM_001075142.1).

DETAILED DESCRIPTION OF THE INVENTION

Figure 1:
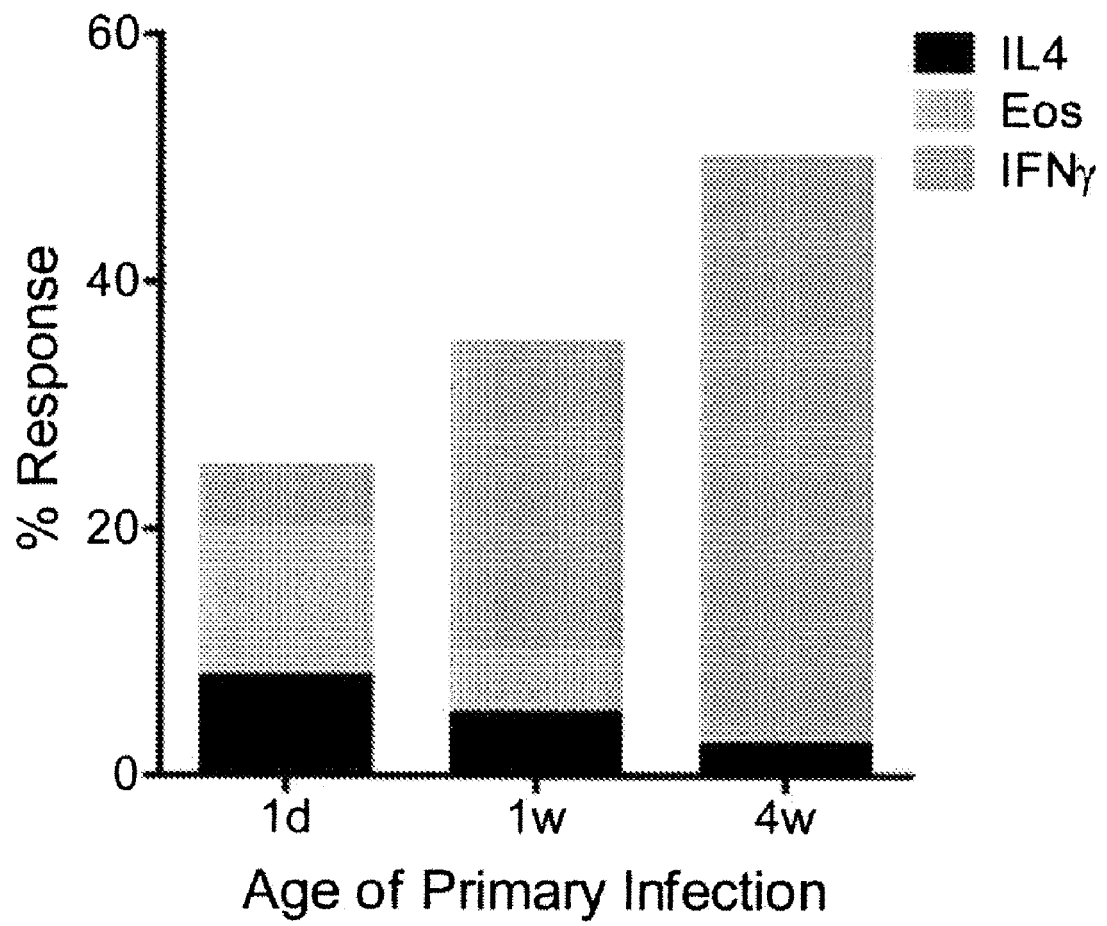
FIG. 1 is adapted from Culley, et al. 2002, and shows that age at initial RSV infection predicts immune response to re-challenge with RSV.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

In humans, RSV bronchiolitis is associated with wheeze/asthma in later life. In infant mice, where the pulmonary and immune systems are still developing, a very transient RSV infection initiates "immunological events" that produce long-term effects on subsequent immune responses and pulmonary function. This closely mimics observations from human children hospitalized for severe RSV-induced bronchiolitis as infants, and demonstrates the relevance of results from the mouse model to human infant RSV infections. Together, these data suggest that infant RSV infection initiates immunological and physiological changes that are determined both by the pathogen itself and by a critical window of immaturity of the immune system. The prior art does not suggest, though, how the long-term effects caused by RSV infection during the critical period might be prevented, nor does it suggest use of an IL-4Rα ASO to prevent RSV-induced asthma. As the present invention demonstrates, protection during this critical window of immunological immaturity provides long-term benefits in attenuating subsequent airway dysfunction.

A correlation between RSV infection and wheeze/asthma has been noted previously, but identifying the causes of this connection—and the potential therapeutic avenues—has proven elusive. The most commonly-accepted models for studying this link use adult animals, yet the adult lung and the adult immune system are markedly different from those of the infant. By comparing infant and weanling mouse models of RSV infection, the present inventor has demonstrated that RSV infection in infants selectively induces pulmonary inflammation and permanently alters airway function (Becnel D, et al., 2005. You D, et al., 2006). In contrast, RSV infection of weanlings (3 wk of age) elicits only transient airway inflammation and airway hyperresponsiveness (Becnel D, et al., 2005.). These data help to explain human epidemiological data, which indicated that early infection with RSV—if severe enough to require hospitalization—is correlated with the development of persistent wheeze and childhood asthma (Sigurs N. *Am J Respir Crit Care Med.* 2001; 163:S2-6.). Most human children have been infected by RSV at least once, before their second birthday. However, the timing and severity of that initial infection varies considerably. Some children (including newborns and infants) develop severe disease and require hospitalization, while others do not. Those requiring hospitalization, though, are most often newborns and infants. The present inventor's data and that of others (Culley F J, et al., 2002. Sigurs N., 2001. Dakhama A, et al. *J Immunol.* 2003; 175:1876-83.) suggest that one's age at initial RSV infection is a critical risk factor associated with subsequent development of wheeze/asthma and subsequent T-cell immune responses upon later RSV re-infection.

The present inventor has also shown that if mice are infected with RSV as infants, and then subsequently exposed to allergen as adults, they develop an "asthma-like" response including enhanced airway resistance, mucus hyperproduction, enhanced Th2 cytokine production (mainly IL-4, -5, and -13 in the BALF and eosinophilia (You D, et al., 2006). Culley, et al. clearly demonstrated that age of initial infection is also important in determining subsequent T-cell memory, with infection of infants resulting in a largely Th2 polarized T-cell memory response (Culley F J, et al., 2002). The present inventor extended that observation by demonstrating that age at initial infection is critically important in determining the immuno-physiologic response to RSV and may explain why some children develop long-term wheeze/asthma following RSV bronchiolitis and others do not.

Figure 2:
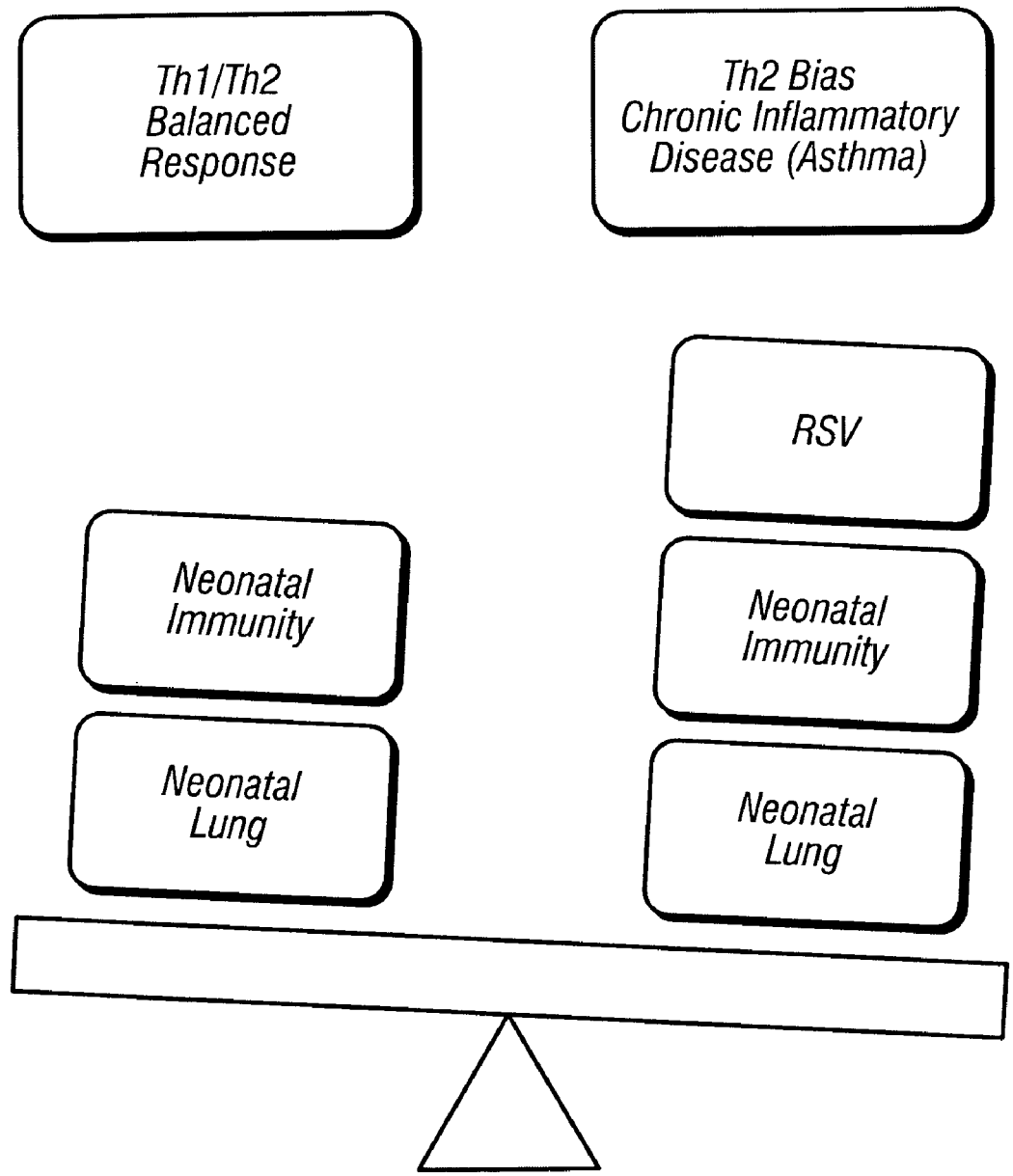
FIG. 2 shows schematically that infection with RSV induces a skewed immune response biased toward Th2 cells, and away from a balanced Th1/Th2 response.
Figure 3:
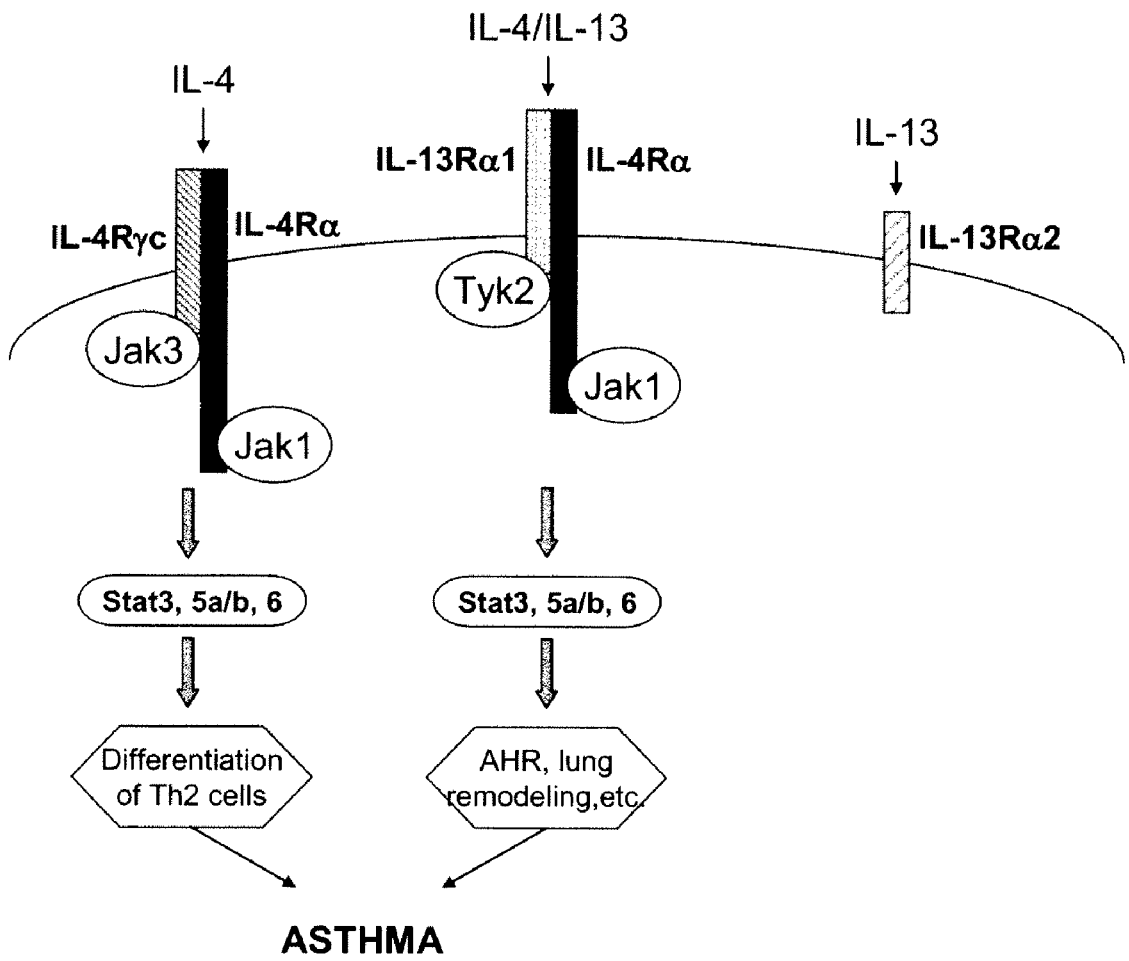
FIG. 3 shows the relationship between IL-4Rα and other receptors of the interleukin-4 and -13 receptor families, as well as the downstream effects of IL-4 and IL-13 signaling via heterodimers comprising IL-4Rα.

The present inventor extended the observations of Culley, et al. by assessing lung pathology, airway responsiveness, and cytokine production after primary infection of weanling (21 days of age) and infant mice (7 days of age) (Becnel D, et al., 2005. You D, et al., 2006). Mice infected with RSV as infants (7 days of age) demonstrated altered pulmonary function and pathology as adults (103 d of age), which was exacerbated when combined with subsequent allergen exposure (Becnel D, et al., 2005. You D, et al., 2006). Mice infected during infancy exhibited long-term pulmonary inflammation, enhanced levels of IL-13, increased amounts of mucus-production, and significant airway remodeling (You D, et al. 2006). In contrast, there was no evidence of airway hyperresponsiveness in adult mice infected with RSV as weanlings (21 days of age), and after the infection resolved the lungs were pathologically similar to the lungs from control mice (i.e. no evidence of mucus production, pulmonary inflammation, or subepithelial fibrosis). Furthermore, delaying the age of primary infection (3 wk vs. <1 wk) protected against the subsequent development of airway resistance upon re-infection, which was correlated with a significant reduction in pulmonary IL-13 levels compared to mice infected as infants (Becnel D, et al., 2005. You D, et al., 2006). Cumulatively, these findings suggest that RSV infection in infants elicits a Th2 immune response and establishes a Th2-biased memory response to subsequent infections and perhaps to other viruses or antigens (se, e.g., FIG. 2). The mechanisms underlying the diminished capacity of the infant immune system to develop a Th1 immune response to RSV and to resist re-infection remain, at best, poorly understood.

The IL-4Rα antisense oligonucleotides are administered once daily for two days prior to infection of the infant with RSV and through two days after RSV infection. Both IL-4Rα antisense oligonucleotides and RSV are administered intranasally (i.n.). Data from this inventor's studies in mice suggest that employing IL4Rα-ASO as a vaccine strategy prevents RSV-induced bronchiolitis and the subsequent development of wheeze and/or asthma associated with infantile RSV infection, since RSV bronchiolitis induces long-term wheeze or asthma predominantly when acquired by human infants. Therefore, timing of vaccine administration is critical. The IL-4Rα antisense oligonucleotide used in the inventor's initial studies is targeted to nucleotides 1411-1421 (located in exon 11) of the mouse IL-4Rα gene (e.g., NCBI Accession No. NM_001008700). Karras, et al. reported administration of this IL-4Rα ASO as an aerosol directly to the lungs of adult mice to relieve symptoms of asthma in an acute ovalbumin (OVA) challenge model of allergic asthma, but the present invention discloses the surprising finding that intranasal administration of IL-4Rα ASO to infant mice may prevent susceptibility to RSV-related asthma in the first instance.

In addition, non-human variants of RSV also exist and cause similar respiratory sequelae. For example, bovine RSV is a major concern in the cattle industry, ovine RSV in the sheep industry, and caprine RSV in the goat industry (Stott E J & Taylor G, *Arch Virol* 1985; 84(1-2):1-52). We therefore anticipate that application of this same vaccine strategy (IL-4Rα antisense oligonucleotides+RSV) will prevent RSV-induced bronchiolitis and the development of subsequent wheeze associated with infantile RSV infection.

IL-4Rα signaling is important in regulating the infant immune response to RSV. The amount of IL-13 in the BALF of infant mice infected with RSV is significantly elevated. In both humans and animal models, IL-13 has been implicated in multiple pathologies associated with allergies and asthma, including the development of airway hyperreactivity (AHR), lung remodeling, and mucus hyperproduction. IL-13 signals through the type II IL-4 receptor (IL-4R), a heterodimeric complex, composed of the IL-4Rα and IL-13Rα1 chains. Although a second IL-13 receptor exists, IL-13Rα2, it is currently thought to be a "decoy" receptor acting to negatively regulate IL-13 signaling. We hypothesized that inhibition of IL-4Rα would inhibit (or substantially reduce) the initiation of a Th2 immune response in our infant RSV infection model and reduce the development of AHR in these mice. Furthermore, suppressing IL-4 signaling through IL-4Rα may allow for an increased Th1 immune response to infant RSV infection initially and upon subsequent re-infection as an adult.

EXAMPLE 1

IL-4Rα ASO therapy protects mice against the development of RSV-induced airway hyperreactivity.

Figure 4:
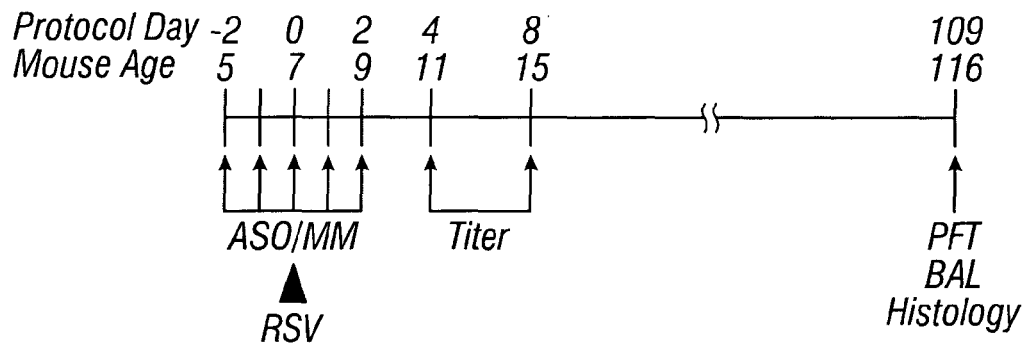
FIG. 4 shows a schematic of the experimental protocol used to study the role of IL-4Rα in the induction of Th2 skew and pulmonary dysfunction associated with infantile RSV infection. Mice were treated with IL4-Rα antisense oligonucleotide (ASO) or an IL-4Rα mismatch oligonucleotide (MM), and initially infected with RSV at 7 days of age.
Figure 5:
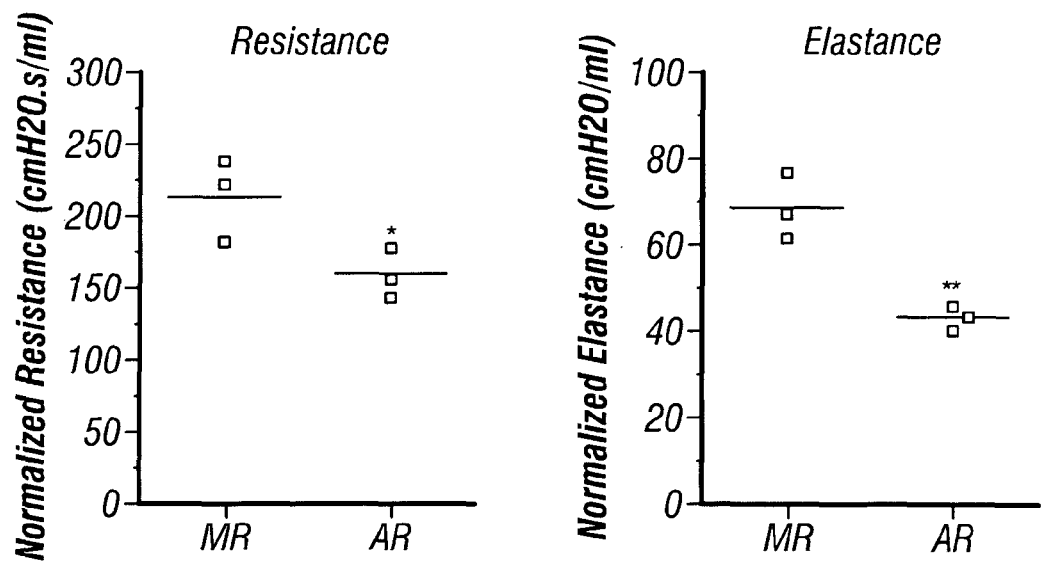
FIG. 5 shows the effect of IL-4Rα ASO therapy on pulmonary function. Mice receivin IL-4Rα ASO therapy (AR) demonstrated reduced airway resistance and elastance following infantile RSV infection as compared to mismatch ASO (MR) treated animals. Lung function was measured at 109 dpi. Data are plotted as percent change over baseline. Significant difference compared with MR values (*: $p<0.05$; **: $p<0.01$). MR and RSV groups were not statistically different (n=3).

Mouse IL-4Rα ASO were designed, screened for inhibition of target mRNA, and provided by Isis Pharmaceuticals. The mouse IL-4Rα ASO 5'-CCGCTGTTCTCAGGTGA-CAT-3' (SEQ ID NO:3) and an IL-4Rα mismatch ASO 5'-CCACTCATCACTGCTGACTT-3' (SEQ ID NO:4) were each synthesized with chimeric design, wherein nucleotides 1-5 and 16-20 are 2'-O-methoxyethyl nucleotides, nucleotides 6-15 are 2'-deoxynucleotides, every internucleoside linkage is a phosphorothioate linkage, and every cytidine residue is a 5-methyl cytidine. Seven day old BALB/c mice were inoculated intranasally (i.n.) with RSV (RSV group), while cohorts of mice were treated with either IL-4Rα ASO (AR group,) or a 7-base mismatch control oligonucleotides (MR group). The oligonucleotides were administered i.n. at a dose of 100 µg/kg once daily, starting two days before RSV infection and continuing through two days after infection (FIG. 4). Prior to infection, mice were anesthetized with isoflurane (induction at 3% isoflurane and maintenance, if necessary, at 0.5% isoflurane). The mice were held upright with the neck fully extended. A 10 µl drop of RSV ($2\times10^5$ $TCID_{50}$/g body weight) or vehicle (as sham control) was placed over nostrils with a micropipette (i.n. infection), which the mice readily inhaled. The same procedure and volume were used for i.n. administration of ASO or MM. In this manner, the following three groups of mice were generated and allowed to mature: 1) RSV infected mice (RSV); 2) RSV infected mice treated with IL-4Rα ASO (AR); and 3) RSV infected mice treated with MM ASO (MR). Once mature, on protocol day 109, pulmonary function testing was performed. Briefly, lung resistance to methacholine (MeCh, 2-acetyloxypropyl-trimethyl-azanium, CAS No. 55-92-5, 50 mg/mL in isotonic saline) was assessed using the forced oscillation technique as previously described (Becnel D, et al. 2005. You D, et al. 2006.). Anesthetized mice were mechanically ventilated with a tidal volume of 10 ml/kg and a frequency of 2.5 Hz using a computer controlled piston ventilator (FlexiVent, SQREQ; Montreal, Canada). Lung resistance and elastance data were collected and analyzed using the single compartment model, normalized to baseline lung resistance/elastance for each mouse, and plotted as the normalized resistance/elastance. Baseline measurements were obtained for each mouse after inhalation of saline. The mice that received IL-4Rα ASO as infants exhibited improved lung function (i.e. decreased airway resistance and decreased elastance) compared with infant control mice infected with RSV and with infant mice treated with the MM ASO (FIG. 5). No difference in airway response was found between RSV infected mice either treated or not treated with MM ASO.

EXAMPLE 2

IL-4Rα ASO therapy reduces CD4+ T lymphocyte numbers following infant RSV infection.

Lymphocytes were isolated from whole lung homogenates at 10 dpi, stained for CD3, CD4, and CD8, and analyzed by flow cytometry. Mice receiving IL-4Rα ASO therapy (AR) demonstrated significantly reduced CD4+ T cell numbers ($p<0.05$) following infant RSV infection as compared to mismatch IL-4Rα ASO treated animals (MR) and to RSV-infected animals receiving no ASO (RSV).

EXAMPLE 3

IL-4Rα ASO therapy reduces pulmonary inflammation following infant RSV infection.

Figure 7:
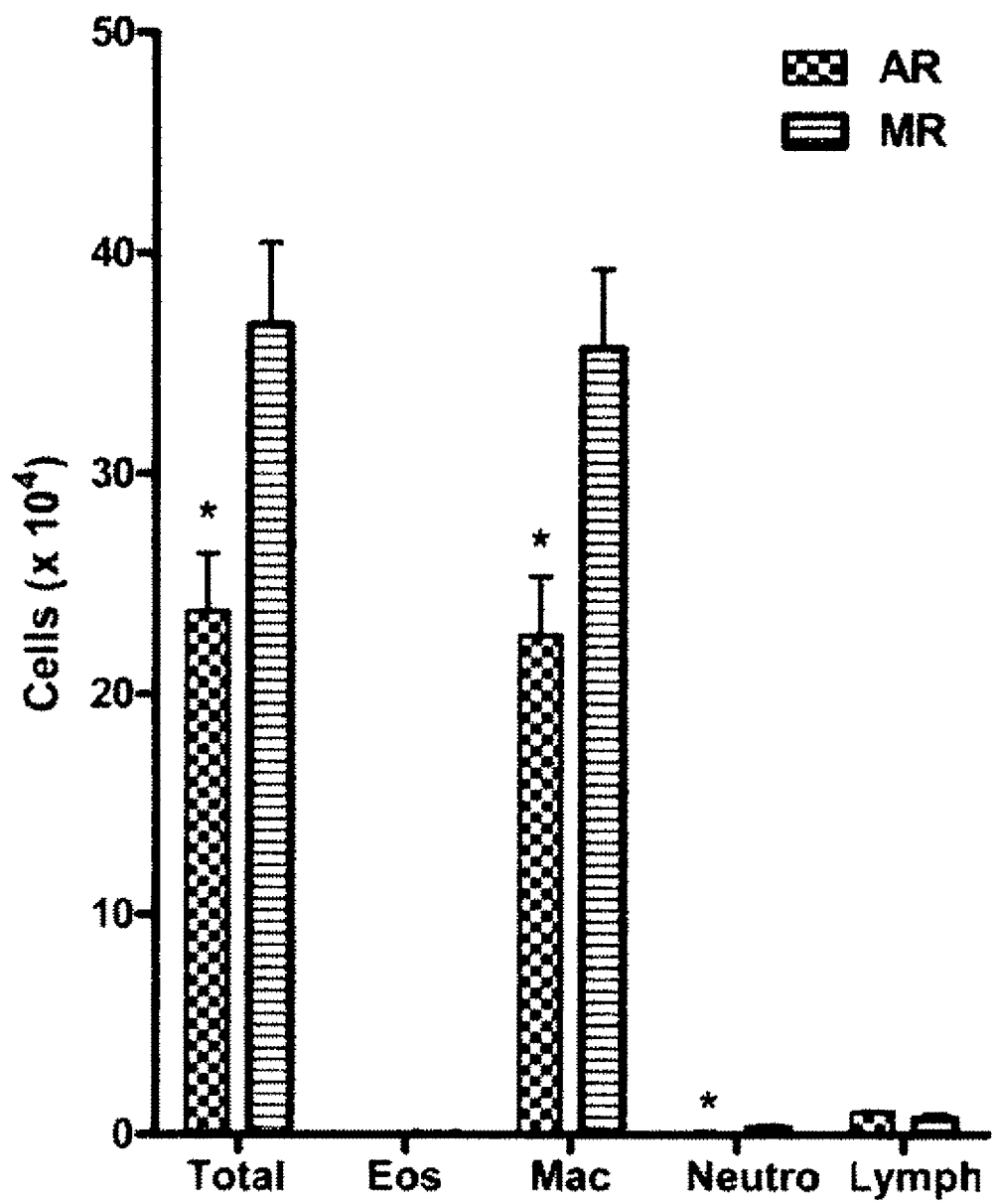
FIG. 7 shows that IL-4Rα ASO therapy reduced airway inflammation. Bronchoalveolar lavage fluid (BALF) was isolated at 1 dpi. Data are expressed as mean±SEM. Significant difference compared with RSV values (*p: $p<0.05$).
Figure 8:
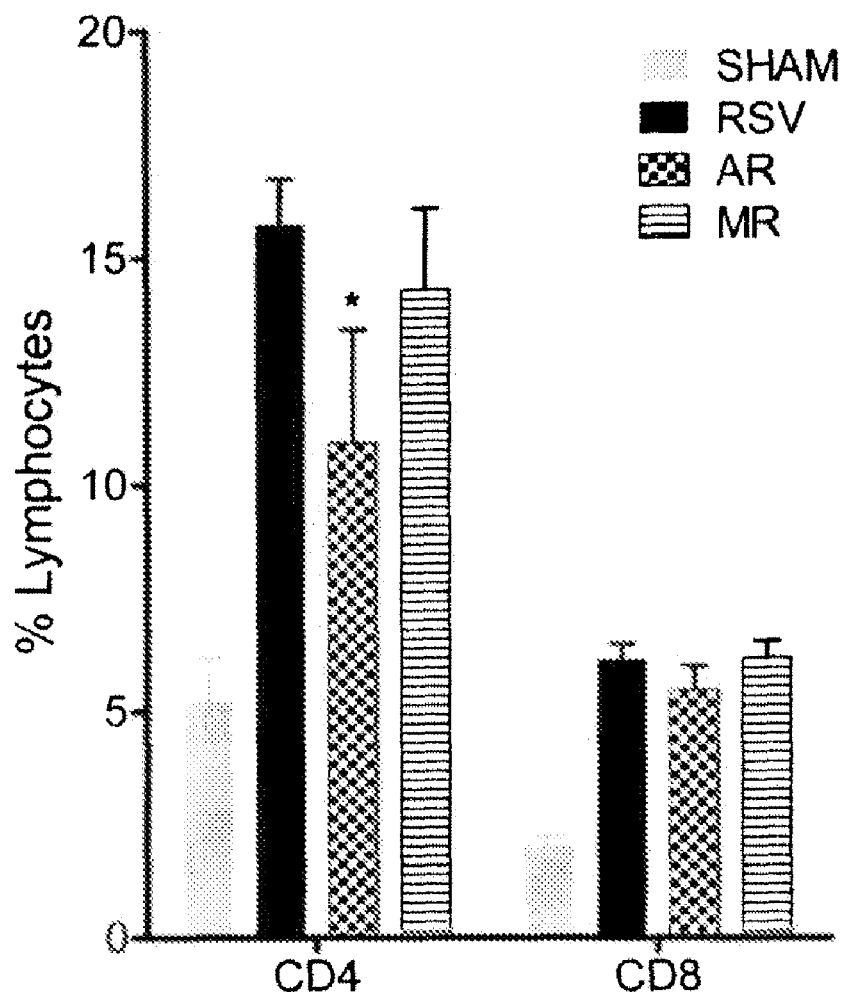
FIG. 8 shows that IL-4Rα ASO therapy reduced CD4+ T lymphocyte numbers in the lung following infantile RSV infection. Infant mice were treated with IL-4Rα ASO (AR group) or IL-4Rα MM (MR group) or saline (RSV group) and then initially infected with RSV at 7 days of age. As a control, infant mice were also sham infected (Sham group). Lung cells were isolated at 10 dpi. Data are expressed as mean±SEM. Significant difference compared with RSV values (**: $p<0.05$).

The above data indicated that pulmonary inflammation might be reduced in the mice treated with IL-4Rα ASO. Therefore, we isolated BALF from each group of mice at 1 dpi. We found that the number of lymphocytes in the BALF was significantly decreased in the IL-4Rα ASO treated mice (AR) compared with either the RSV group (FIG. 7) or the RSV/MR group. Infant RSV infection predominantly induces a mononuclear cell infiltration of the BALF and, interestingly, IL-4Rα ASO treatment reduced this population of cells the most. Furthermore, IL-4Rα ASO treatment induced a slight increase in the number of neutrophils recruited to the BALF compared to RSV infection alone ($3.66\times10^4 \pm 1.27\times10^3$ vs. $1.69\times10^4 \pm 5.77\times10^3$; mean±SEM).

EXAMPLE 4

IL-4Rα ASO therapy reduces RSV-induced Th2 cytokine levels in BALF.

Figure 9:
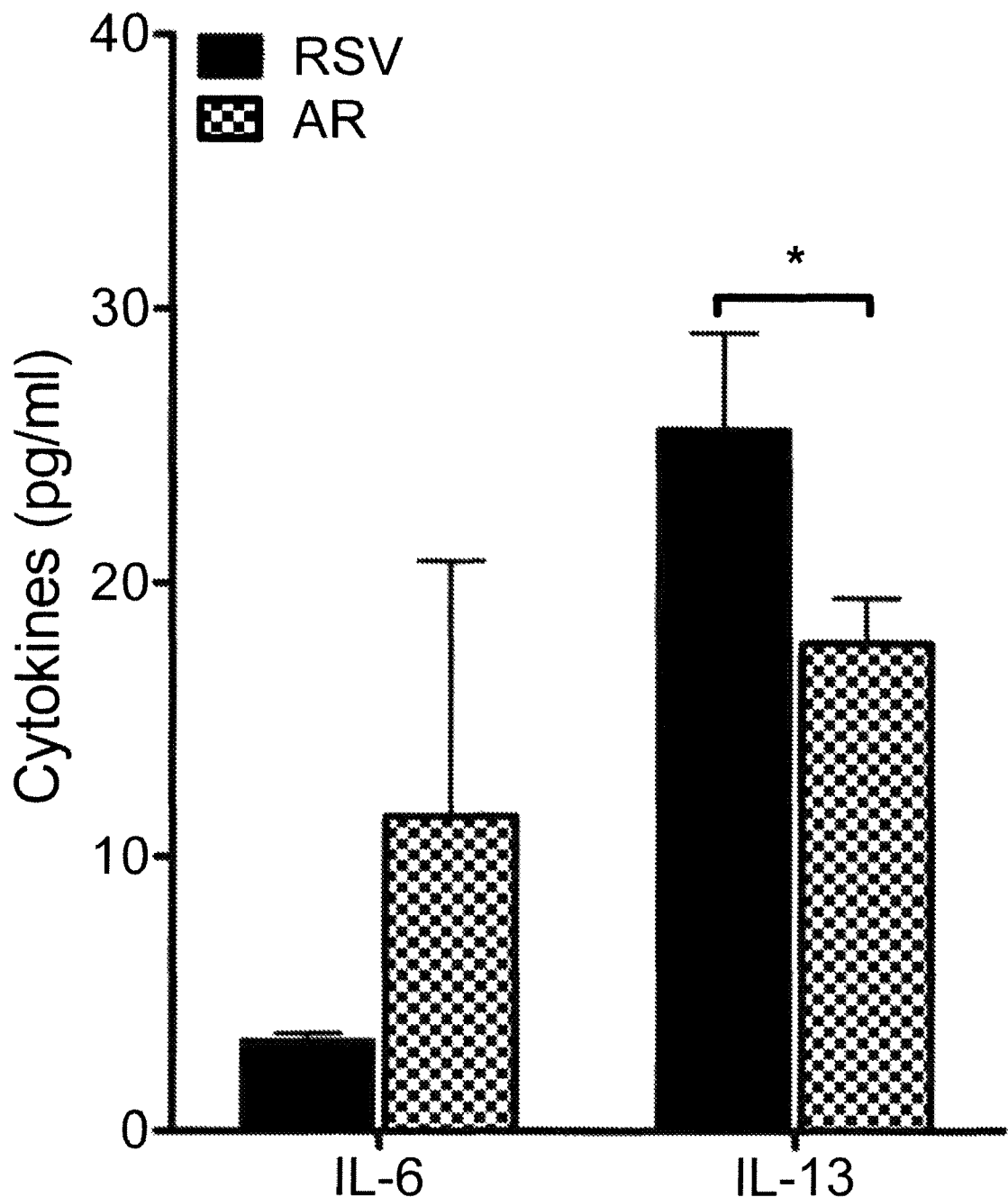
FIG. 9 shows that IL-4α ASO therapy alters expression of cytokine IL-13 in BALF, following RSV infection. BALF was isolated at 1 dpi. Data are expressed as mean±SEM (n=3). Significant difference compared with RSV values (*: $p<0.05$).

To explore the mechanism(s) responsible for the anti-inflammatory activity and improved lung function following treatment of RSV-infected infants with IL-4Rα ASO, we quantified Th2 cytokines, including IL-4, IL-5, IL-6, and IL-13 and the Th1 cytokine, IFN-γ, in the BALF at 1 dpi. Cytokine levels were measured from 50 µL of cell-free BALF using a high-throughput multiplex cytokine assay system (X-Plex Mouse Assay, BioRad) according to the manufacturer's instructions. Each sample was analyzed in triplicate on the Bio-Plex 200 system (BioRad). A broad sensitivity range of standards ranging from 1.21 to 37,312 µg/mL (depending on the analyte) was used to quantitate a dynamic range of cytokine concentrations, and to provide the greatest sensitivity. The concentrations of analytes in these assays were quantified using a standard curve, and a 5-parameter logistic regression was performed to derive an equation that was used to predict the concentration of the unknown samples. IL-13 levels were significantly decreased in the BALF, while IL-6 levels appeared to increase following treatment with IL-4Rα ASO (FIG. 9). Data for IL-4, IL-5, and IFN-γ are not displayed because they were below the level of sensitivity for this assay at this time point. The elevation of IL-6 is particularly interesting because it has been shown to increase lung branching in the fetus (Nogueira-Silva C, et al. *Pediatr Res.* 2006; 60:530-36.) and possibly provides a mechanism by which the immune system hastens the development of the lung.

EXAMPLE 5

IL-4Rα ASO therapy reduces pulmonary pathologies associated with infant RSV infection.

Figure 6:
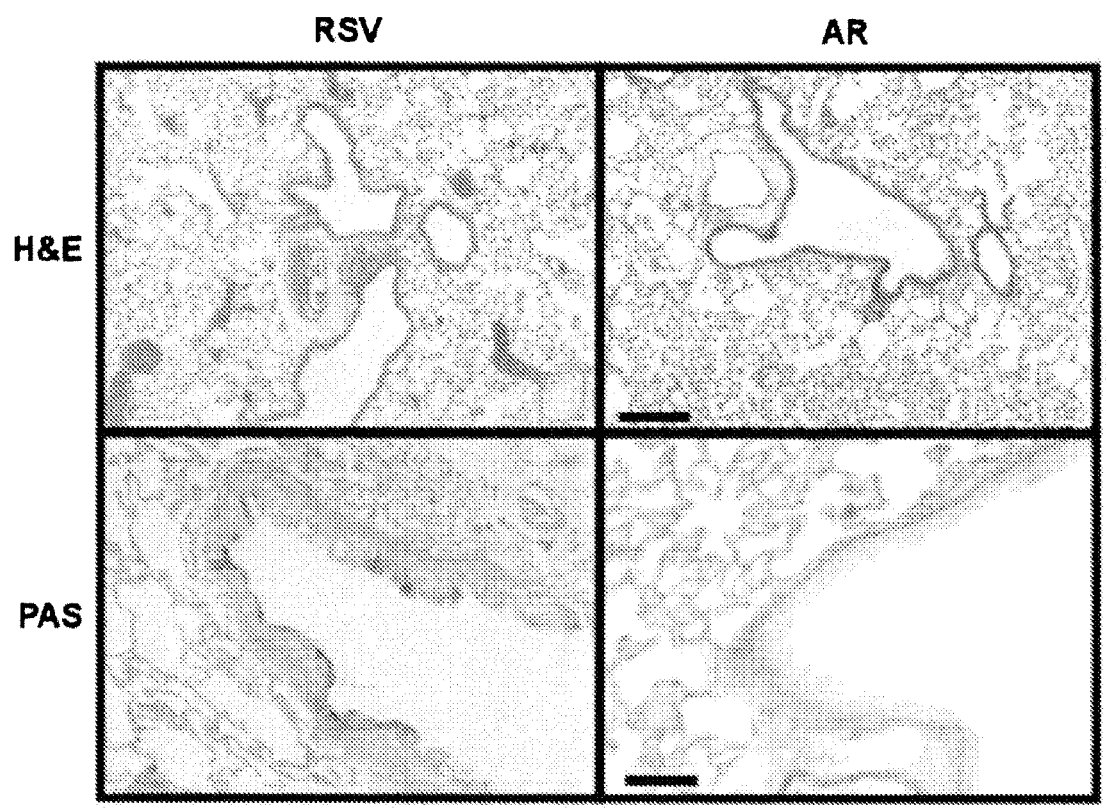
FIG. 6 shows lung histopathology demonstrating airway structure and pulmonary inflammation (hematoxylin and eosin, H&E) and mucus production (periodic acid-Schiff, PAS) at 116 dpi. Scale bar=50 µm (H&E) or 200 µm (PAS).

Mouse lung histopathology was assessed at 109 dpi. IL-4Rα ASO therapy seemed to abolish mucus hyperproduction in the airways and to decrease peribronchiolar and perivascular lymphocytic infiltration (FIG. 6). This data is in contrast to age-matched controls animals that were infected with RSV as infants and developed moderate pulmonary inflammation and exhibited significant mucus hyperproduction.

EXAMPLE 6

IL-4Rα ASO vaccination is correlated with improved pulmonary function after secondary RSV infection.

Figure 10:
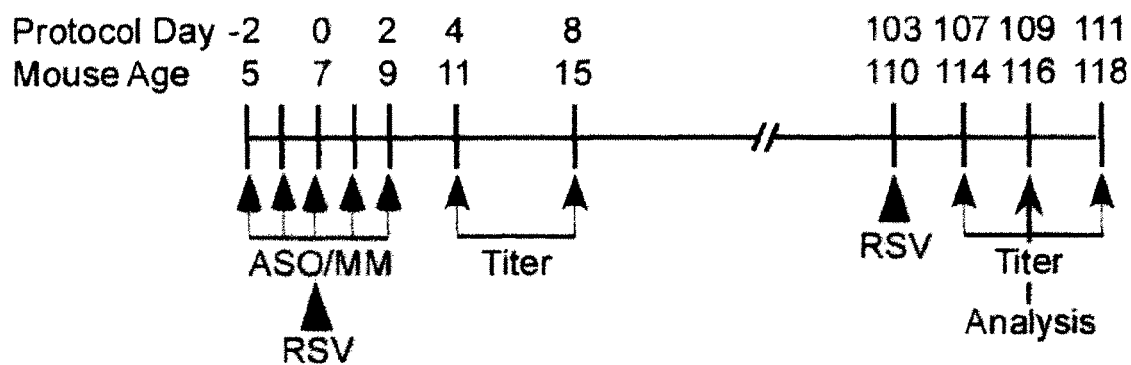
FIG. 10 shows a schematic of the experimental protocol used to study the ability of the IL-4Rα ASO vaccine strategy to inhibit the Th2 response and pulmonary dysfunction associated with secondary infections with RSV. Mice were treated with IL-4Rα ASO or IL-4Rα MM and then initially infected at 7 days of age. Secondary infections were performed on protocol day 103, when the mice had matured to adults.
Figure 11A:
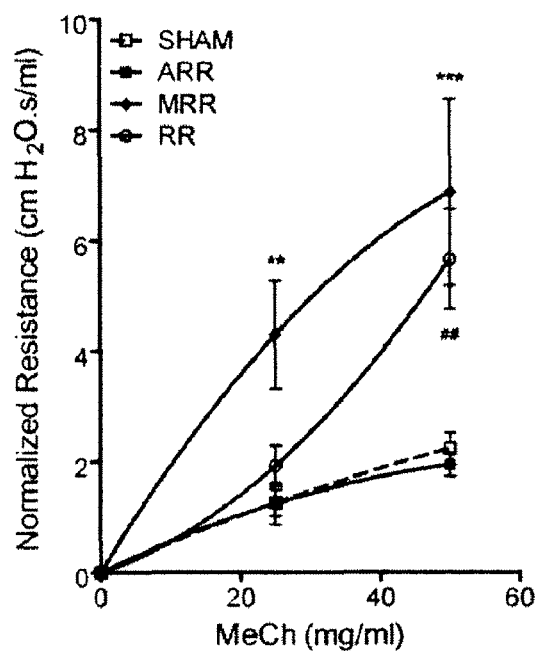
FIG. 11 shows the effect of IL-4Rα ASO therapy on pulmonary function following secondary RSV infection. Mice receiving IL-4Rα ASO therapy (ARR) demonstrated reduced airway resistance (FIG. 11A) and elastance (FIG. 11B) following secondary RSV infection as compared to MM (MRR) treated animals or mice receiving RSV only (RR). Lung function was measured at 111 dpi. Data were normalized to baseline. Significant difference compared with MRR values (*:p<0.05; **:p<0.01). Sham and ARR groups were not statistically different (n=3).
Figure 11B:
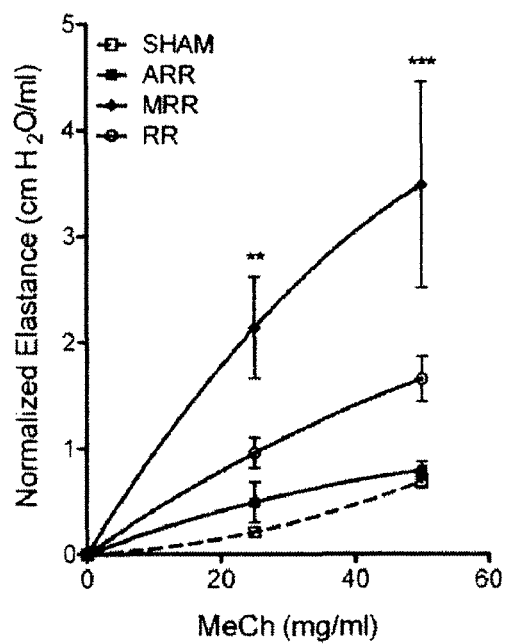

FIG. 10 shows a schematic of the experimental protocol used to study the ability of the IL-4Rα ASO vaccine strategy to inhibit the Th2 response and pulmonary dysfunction associated with secondary infections with RSV. Mice were treated daily with IL-4Rα ASO or IL-4Rα MM from 5 to 9 days of age and were initially infected with RSV at 7 days of age (protocol day zero). Viral titer was measured 4 and 8 days post-infection, to ensure that infection had occurred. Secondary RSV infections were performed on protocol day 103, by which time the mice had matured to adults. Viral titer was measured again on protocol days 107 and 111, and lung functional analyses were performed on protocol day 109. As seen in FIG. 11, IL-4Rα ASO therapy administered during initial RSV infection of infant mice produces significant beneficial effects when these mice are re-infected with RSV as adults. On protocol day 109, lung resistance to increasing doses of methacholine (MeCh; 0, 12.5, 25, and 50 mg/ml in isotonic saline) was assessed using the forced oscillation technique as previously described (Becnel D, et al. 2005. You D, et al. 2006.). Anesthetized mice were mechanically ventilated with a tidal volume of 10 mL/kg and a frequency of 2.5 Hz using a computer controlled piston ventilator (FlexiVent, SCIREQ; Montreal, Canada). Lung resistance and elastance data were collected and analyzed using the single compartment model, normalized to baseline lung resistance/elastance for each mouse, and plotted as the normalized resistance/elastance. Baseline measurements were obtained for each mouse after inhalation of saline. Upon re-infection with RSV, mice that had received IL-4Rα ASO therapy during the initial RSV infection (ARR) demonstrated dramatically reduced airway resistance (FIG. 11A) and reduced airway elastance (FIG. 11B) when compared to mice treated with mismatch IL-4Rα ASO (MRR) or to mice receiving RSV alone (RR). The airway resistance and elastance profiles for ARR mice were not significantly different from the profiles of the sham-infected mice (SHAM).

Although IL-4Rα protein sequences of different species are not identical, they share regions of marked sequence conservation. Most notably, the region about amino acids 76-78 of *H. sapiens* IL-4Rα (SEQ. ID NO:5) shares significant homology with macaque (SEQ ID NO:6), mouse (SEQ. ID NO:7) and bovine (SEQ ID NO:8) IL-4Rα proteins, as shown by the boxed region of the protein sequence alignments of FIG. 12, as well as with the corresponding regions from IL-4Rα protein sequences of other species (e.g., *Pan troglodytes*, not shown). In addition, this region is implicated in atopic asthma (Deichmann K, et al. *Biochem Biophys Res Commun.* 1997; 231:696-97. Mitsuyasu H, et al. *Nat Genet.* 1998; 19:119-20. Noguchi E, et al. *Am J Respir Crit Care Med.* 1999; 160:342-45.). As disclosed in published U.S. patent application publication no. 2007/0161594 (corresponding to U.S. patent application Ser. No. 11/548,657), antisense oligonucleotides targeted to human IL-4Rα may inhibit human IL-4Rα mRNA to differing degrees. In particular, antisense oligonucleotides targeted about the regions including nucleotides 167 to 265 (containing the transcription and translation start sites) and 357 to 515 of SEQ ID NO:1 may be particularly useful for inhibiting human IL-4Rα mRNA (se, e.g., Id at Table 5). Consequently, antisense oligonucleotides targeted to human IL-4Rα are expected to be useful for the methods of this invention, generally, and antisense oligonucleotides targeted to nucleotides 167 through 265 (containing the transcription and translation start sites) and 357 through 515 of SEQ ID NO:1 are expected to be particularly useful for the methods of this invention. Because RSV infects animals other than humans (including, but not limited to cows, sheep, and goats), and because these other animals also express IL-4Rα proteins, antisense oligonucleotides directed at the IL-4Rα sequences of other animals—and particularly at those regions with homology to nucleotides 167 to 265 (e.g., containing the transcription and translation start sites of the non-human IL-4Rα sequences) and 357 to 515 of SEQ ID NO:1—may also be useful for the methods of this invention. In particular, for non-human primates those regions are nucleotides 89-154 and 279-437 of SEQ ID NO:9, and for bovines those regions are nucleotides 37-135 and 227-385 of SEQ ID NO:10.

EXAMPLE 7

IL-4Rα ASO therapy protecting human infants against development of RSV-induced airway hyperreactivity.

Human IL-4Rα ASOs are designed to target different regions of human IL-4Rα, and screened for inhibition of IL-4Rα RNA. Each human IL-4Rα ASO is 20 nucleotides in length (a 20-mer), with chimeric design, wherein nucleotides 1-5 and 16-20 are 2'-O-methoxyethyl nucleotides, nucleotides 6-15 are 2'-deoxynucleotides, every internucleoside linkage is a phosphorothioate linkage, and every cytidine residue is a 5-methyl cytidine. Infant humans with symptoms of RSV infection or with active RSV infection (e.g., as shown by a test for RSV) are given at least one human IL-4Rα ASO intranasally at a dose of 1 µg/kg to 500 µg/kg at least once, and optionally once daily thereafter for as long as clinical signs of active RSV infection are evident (e.g., by detection of viral antigens, viral mRNA, or a rise in serum antibodies, by isolation of the virus, or by a combination of these strategies).

IL-4Rα ASO therapy protecting infant cattle against development of RSV-induced airway hyperreactivity.

Bovine IL-4Rα ASOs are designed to target different regions of bovine IL-4Rα, and screened for inhibition of IL-4Rα RNA. Each bovine IL-4Rα ASO is 20 nucleotides in length (a 20-mer), with chimeric design, wherein nucleotides 1-5 and 16-20 are 2'-O-methoxyethyl nucleotides, nucleotides 6-15 are 2'-deoxynucleotides, every internucleoside linkage is a phosphorothioate linkage, and every cytidine residue is a 5-methyl cytidine. Infant bovines with symptoms of bovine RSV infection or with active bovine RSV infection (e.g., as shown by a test for bovine RSV) are given at least one bovine IL-4Rα ASO intranasally at a dose of 1 μg/kg to 500 μg/kg at least once, and optionally once daily thereafter for as long as clinical signs of active bovine RSV infection are evident (e.g., by detection of viral antigens, viral mRNA, or a rise in serum antibodies, by isolation of the virus, or by a combination of these strategies).

Data from the inventor's preliminary studies using IL-4Rα ASO in infant mice suggest that employing IL-4Rα ASO in infant humans as a part of a novel vaccine strategy could prevent RSV-induced bronchiolitis and the development of subsequent wheeze and/or asthma associated with severe infant RSV infection. This is evidenced in infant mice by the overall improvement in lung function, which correlated with decreases in RSV-induced pulmonary inflammation, mucus production, and IL-13 levels in bronchoalveolar lavage fluid. Furthermore, the inventor's data also suggest a role for IL-13 in RSV-induced airway dysfunction. This is in contrast to the study performed by Park and colleagues (Park J W, et al. *J Allergy Clin Immunol.* 2003; 112:1078-87.), which showed no role for IL-13 in primary RSV infection of adult BALB/c mice. In sum, this inventor's data suggest that interventional therapy with ASOs targeted to human IL-4Rα and administered to infant humans during initial RSV infection may be of significant benefit, preventing childhood wheeze and potentially life-long lung dysfunction.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only, the scope of the present invention is to be limited only by the following claims.

The invention claimed is:

1. A method, comprising: immunizing a subject against pulmonary inflammation and airway hyperresponsiveness associated with infantile respiratory syncytial virus infection by administering an antisense oligonucleotide to a subject, wherein:
   a) the subject is an infant and said antisense oligonucleotide is administered as part of a respiratory syncytial virus vaccination;
   b) said antisense oligonucleotide is between 10 and 40 nucleotides in length;
   c) said antisense oligonucleotide is targeted to a nucleic acid molecule encoding IL-4Rα;
   d) the first 5 and last 5 nucleotides at the 5' and 3' ends of the antisense oligonucleotide are 2'-O-methoxyethyl nucleotides, the nucleotides between the first 5 and last 5 nucleotides at the 5' and 3' ends are 2'-deoxynucleotides, every internucleoside linkage is a phosphorothioate linkage, and every cytidine residue is a 5-methylcytidine.

2. The method of claim 1, wherein said antisense oligonucleotide is single-stranded.

3. The method of claim 2, wherein administering an antisense oligonucleotide to the subject is by inhalation.

4. The method of claim 3, wherein the inhalation is nasal inhalation.

5. The method of claim 4, wherein said infant is a human in the first year of life.

6. The method of claim 5, wherein said antisense oligonucleotide is targeted to nucleotides 167-265 of SEQ ID NO:1.

7. The method of claim 6, wherein said antisense oligonucleotide bears at least 75% sequence identity with the complement of nucleotides 167-265 of SEQ ID NO:1.

8. The method of claim 5, wherein said antisense oligonucleotide is targeted to nucleotides 357-515 of SEQ ID NO:1.

9. The method of claim 8, wherein said antisense oligonucleotide bears at least 75% sequence identity with the complement of nucleotides 357-515 of SEQ ID NO:1.

10. The method of claim 4 wherein said infant is a non-human primate in the first 6 months of life.

11. The method of claim 10, wherein said antisense oligonucleotide is targeted to nucleotides 89-154 of SEQ ID NO:9.

12. The method of claim 11, wherein said antisense oligonucleotide bears at least 75% sequence identity with the complement of nucleotides 89-154 of SEQ ID NO:9.

13. The method of claim 10, wherein said antisense oligonucleotide is targeted to nucleotides 279-437 of SEQ ID NO:9.

14. The method of claim 13, wherein said antisense oligonucleotide bears at least 75% sequence identity with the complement of nucleotides 279-437 of SEQ ID NO:9.

15. The method of claim 4, wherein said infant is a bovine in the first 8 weeks of life, and wherein said respiratory syncytial virus is bovine respiratory syncytial virus.

16. The method of claim 15, wherein said antisense oligonucleotide is targeted to nucleotides 37-135 of SEQ ID NO:10.

17. The method of claim 16, wherein said antisense oligonucleotide bears at least 75% sequence identity with the complement of nucleotides 37-135 of SEQ ID NO:10.

18. The method of claim 15, wherein said antisense oligonucleotide is targeted to nucleotides 227-385 of SEQ ID NO:10.

19. The method of claim 18, wherein said antisense oligonucleotide bears at least 75% sequence identity with the complement of nucleotides 227-385 of SEQ ID NO:10.

20. The method of claim 1, wherein the respiratory syncytial virus infection is a primary infection.

21. The method of claim 1, wherein said infant is a human in the six months of life.

22. The method of claim 4, wherein said infant is a human in the six months of life.

23. A method, comprising: blocking the initiation of Th2 cellular differentiation and effector function associated with infantile respiratory syncytial virus infection by administering an antisense oligonucleotide to a subject, wherein:
   a) the subject is an infant and the antisense oligonucleotide is administered as a part of a respiratory syncytial virus vaccination;

b) said antisense oligonucleotide is between 10 and 40 nucleotides in length;
c) said antisense oligonucleotide is targeted to a nucleic acid molecule encoding IL-4Rα;
d) the first 5 and last 5 nucleotides at the 5' and 3' ends of the antisense oligonucleotide are 2'-O-methoxyethyl nucleotides, the nucleotides between the first 5 and last 5 nucleotides at the 5' and 3' ends are 2'-deoxynucleotides, every internucleoside linkage is a phosphorothioate linkage, and every cytidine residue is a 5-methylcytidine.

24. The method of claim 23, wherein the respiratory syncytial virus infection is a primary infection.

* * * * *